(12) United States Patent
Berns

(10) Patent No.: US 10,966,469 B2
(45) Date of Patent: Apr. 6, 2021

(54) NANOADHESION STRUCTURES FOR SPORTING GEAR

(71) Applicant: Under Armour, Inc., Baltimore, MD (US)

(72) Inventor: Jason Berns, Baltimore, MD (US)

(73) Assignee: UNDER ARMOUR, INC., Baltimore, MD (US)

( * ) Notice: Subject to any disclaimer, the term of this patent is extended or adjusted under 35 U.S.C. 154(b) by 1107 days.

(21) Appl. No.: 15/241,643

(22) Filed: Aug. 19, 2016

(65) Prior Publication Data

US 2017/0065006 A1    Mar. 9, 2017

Related U.S. Application Data

(60) Continuation of application No. 13/614,474, filed on Sep. 13, 2012, now abandoned, which is a division of
(Continued)

(51) Int. Cl.
| | |
|---|---|
| *A41D 27/00* | (2006.01) |
| *A41D 13/00* | (2006.01) |
| *A41D 27/24* | (2006.01) |
| *A61F 9/02* | (2006.01) |
| *A63B 33/00* | (2006.01) |
| *B29C 65/00* | (2006.01) |
| *A43B 13/36* | (2006.01) |
| *B29C 65/62* | (2006.01) |

(Continued)

(52) U.S. Cl.
CPC ......... *A41D 13/0015* (2013.01); *A41D 27/20* (2013.01); *A41D 27/24* (2013.01); *A41D 27/28* (2013.01); *A42B 1/048* (2013.01); *A43B 5/00* (2013.01); *A43B 13/12* (2013.01); *A43B 13/186* (2013.01); *A43B 13/223* (2013.01); *A43B 13/36* (2013.01); *A61F 9/026* (2013.01); *A63B 33/002* (2013.01); *B29C 65/62* (2013.01); *B29C 66/1122* (2013.01); *B29C 66/1352* (2013.01); *B29C 66/30321* (2013.01); *B29C 66/43* (2013.01); *B29C 66/431* (2013.01); *B29C 66/472* (2013.01); *B29C 66/729* (2013.01); *A44B 19/08* (2013.01); *A63B 33/004* (2020.08); *A63B 2209/10* (2013.01); *B29C 66/71* (2013.01); *B29K 2105/124* (2013.01)

(58) Field of Classification Search
CPC .... A41D 13/0015; A41D 27/20; A41D 27/24; A41D 27/28
See application file for complete search history.

(56) References Cited

U.S. PATENT DOCUMENTS

| | | | |
|---|---|---|---|
| 2,435,509 A | * | 2/1948 | Pfeffer, Jr. ............... A41B 3/00 2/131 |
| 4,402,146 A | | 9/1983 | Parracho et al. |

(Continued)

*Primary Examiner* — Richale L Quinn
(74) *Attorney, Agent, or Firm* — Edell, Shapiro & Finnan, LLC

(57) ABSTRACT

An apparatus including a first surface configured to attach the apparatus to a second surface of another object, and a plurality of elongated nanofibers. Each nanofiber has one end connected to the first surface and an opposite end extending away from the first surface. The plurality of elongated nanofibers is configured to adhere to the second surface by nanoadhesion when brought into contact with the second surface.

14 Claims, 17 Drawing Sheets

Related U.S. Application Data application No. 12/819,378, filed on Jun. 21, 2010, now Pat. No. 8,424,474.

(60) Provisional application No. 61/218,735, filed on Jun. 19, 2009.

(51) Int. Cl.

| | | |
|---|---|---|
| *A41D 27/20* | (2006.01) | |
| *A41D 27/28* | (2006.01) | |
| *A42B 1/048* | (2021.01) | |
| *A43B 5/00* | (2006.01) | |
| *A43B 13/12* | (2006.01) | |
| *A43B 13/18* | (2006.01) | |
| *A43B 13/22* | (2006.01) | |
| *A44B 19/08* | (2006.01) | |
| *B29K 105/12* | (2006.01) | |

(56) References Cited

U.S. PATENT DOCUMENTS

| | | | |
|---|---|---|---|
| 5,003,902 A * | 4/1991 | Benstock | A41D 27/24 112/402 |
| 5,353,526 A | 10/1994 | Foley et al. | |
| 5,554,146 A * | 9/1996 | Niederhofer | A61F 13/622 604/391 |
| 5,590,615 A * | 1/1997 | Wong | A41D 27/10 112/441 |
| 5,770,529 A | 6/1998 | Dennis et al. | |
| 5,794,359 A | 8/1998 | Jenkins et al. | |
| 5,869,172 A * | 2/1999 | Caldwell | A61F 13/00063 128/849 |
| 5,885,679 A * | 3/1999 | Yasue | A41D 27/24 428/57 |
| 5,946,825 A | 9/1999 | Koh et al. | |
| 6,237,251 B1 | 5/2001 | Litchfield et al. | |
| 6,308,509 B1 | 10/2001 | Scardino et al. | |
| 6,361,861 B2 | 3/2002 | Gao et al. | |
| 6,562,167 B2 | 5/2003 | Coenen et al. | |
| 6,722,026 B1 | 4/2004 | Lent | |
| 6,737,160 B1 | 5/2004 | Full et al. | |
| 6,872,439 B2 | 3/2005 | Fearing et al. | |
| 6,899,945 B2 * | 5/2005 | Smalley | B82Y 30/00 2/2.5 |
| 7,011,723 B2 | 3/2006 | Full et al. | |
| 7,013,818 B2 * | 3/2006 | Zhang | A41D 27/24 112/441 |
| 7,056,409 B2 | 6/2006 | Dubrow | |
| 7,074,294 B2 | 7/2006 | Dubrow | |
| 7,132,161 B2 * | 11/2006 | Knowles | B82Y 10/00 428/364 |
| 7,144,624 B2 * | 12/2006 | Knowles | B82Y 10/00 428/364 |
| 7,175,723 B2 | 2/2007 | Jones et al. | |
| 7,175,762 B1 | 2/2007 | Noca et al. | |
| 7,198,974 B2 | 4/2007 | Forbes | |
| 7,229,685 B2 | 6/2007 | Full et al. | |
| 7,279,916 B2 | 10/2007 | Suhir | |
| 7,455,743 B2 * | 11/2008 | Kramer | A41D 27/245 156/157 |
| 7,479,318 B2 * | 1/2009 | Jagota | B81C 1/00111 428/88 |
| 7,543,399 B2 | 6/2009 | Kilgore et al. | |
| 8,142,700 B2 * | 3/2012 | Sitti | B29C 33/3842 264/139 |
| 2003/0124312 A1 | 7/2003 | Autumn | |
| 2003/0208888 A1 | 11/2003 | Fearing et al. | |
| 2004/0005454 A1 | 1/2004 | Full et al. | |
| 2004/0071870 A1 | 4/2004 | Knowles et al. | |
| 2004/0076822 A1 * | 4/2004 | Jagota | C09J 5/00 428/364 |
| 2004/0206448 A1 * | 10/2004 | Dubrow | A61B 17/00 156/276 |
| 2004/0250950 A1 * | 12/2004 | Dubrow | C09J 5/00 156/276 |
| 2005/0072509 A1 | 4/2005 | Full et al. | |
| 2005/0092414 A1 * | 5/2005 | Jones | B29D 30/66 152/210 |
| 2005/0119640 A1 | 6/2005 | Sverduk et al. | |
| 2005/0148984 A1 | 7/2005 | Lindsay et al. | |
| 2005/0151385 A1 | 7/2005 | Autumn et al. | |
| 2005/0181168 A1 | 8/2005 | Barnes et al. | |
| 2005/0181170 A1 | 8/2005 | Fearing et al. | |
| 2005/0181629 A1 | 8/2005 | Jagota et al. | |
| 2005/0224975 A1 | 10/2005 | Basavanhally et al. | |
| 2005/0263658 A1 | 12/2005 | Fontana et al. | |
| 2005/0271869 A1 | 12/2005 | Jackson | |
| 2005/0271870 A1 | 12/2005 | Jackson | |
| 2006/0005362 A1 | 1/2006 | Arzt et al. | |
| 2006/0065799 A1 | 3/2006 | Fontana et al. | |
| 2006/0073712 A1 | 4/2006 | Suhir | |
| 2006/0078725 A1 | 4/2006 | Fearing et al. | |
| 2006/0122596 A1 | 6/2006 | Dubrow | |
| 2006/0202355 A1 | 9/2006 | Majidi et al. | |
| 2006/0213599 A1 | 9/2006 | Knowles et al. | |
| 2007/0013103 A1 | 1/2007 | Zhang et al. | |
| 2007/0207186 A1 | 9/2007 | Scanlon et al. | |
| 2007/0281567 A1 | 12/2007 | Baychar | |
| 2008/0169059 A1 * | 7/2008 | Messersmith | C08J 7/12 156/249 |
| 2008/0184453 A1 | 8/2008 | Conley et al. | |
| 2008/0229484 A1 | 9/2008 | Baychar | |
| 2008/0308209 A1 * | 12/2008 | Loutfy | B82Y 30/00 156/62.2 |
| 2009/0176056 A1 | 7/2009 | Marin et al. | |
| 2009/0186548 A1 | 7/2009 | Rock et al. | |
| 2009/0220726 A1 | 9/2009 | Liggett et al. | |
| 2009/0324883 A1 | 12/2009 | Gray et al. | |
| 2010/0218298 A1 | 9/2010 | Stattelmann et al. | |

\* cited by examiner

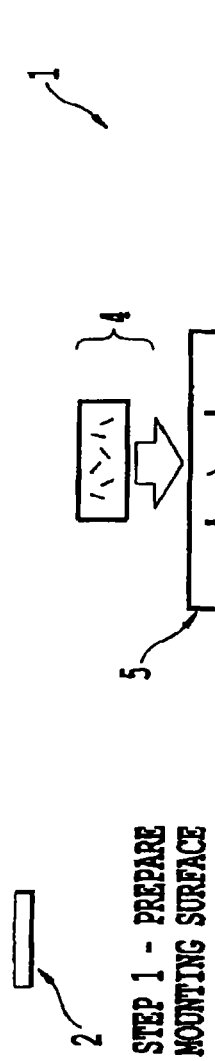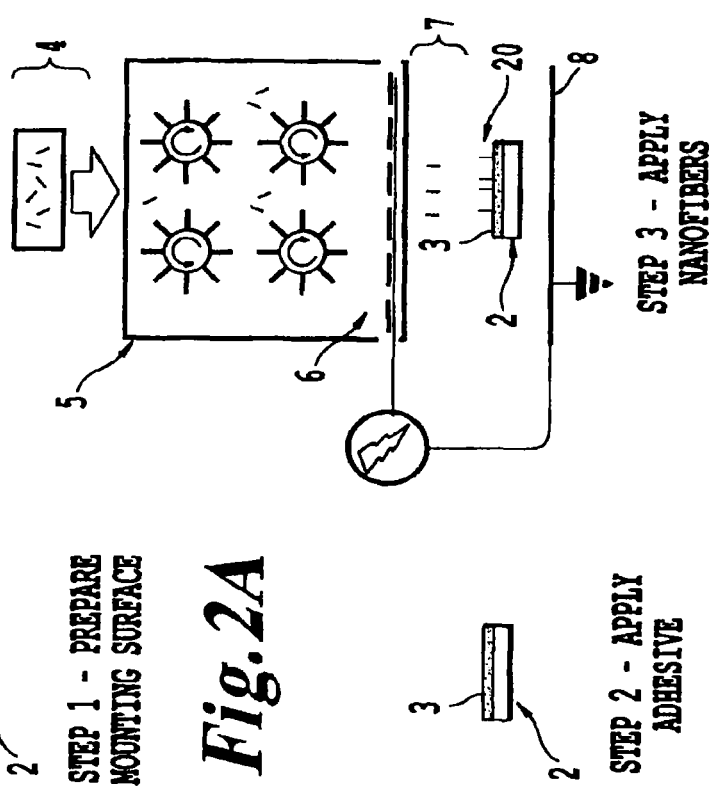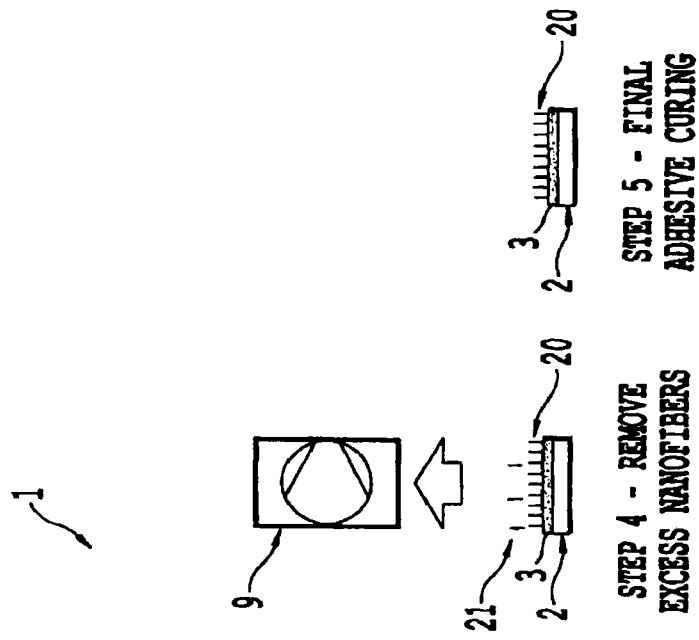

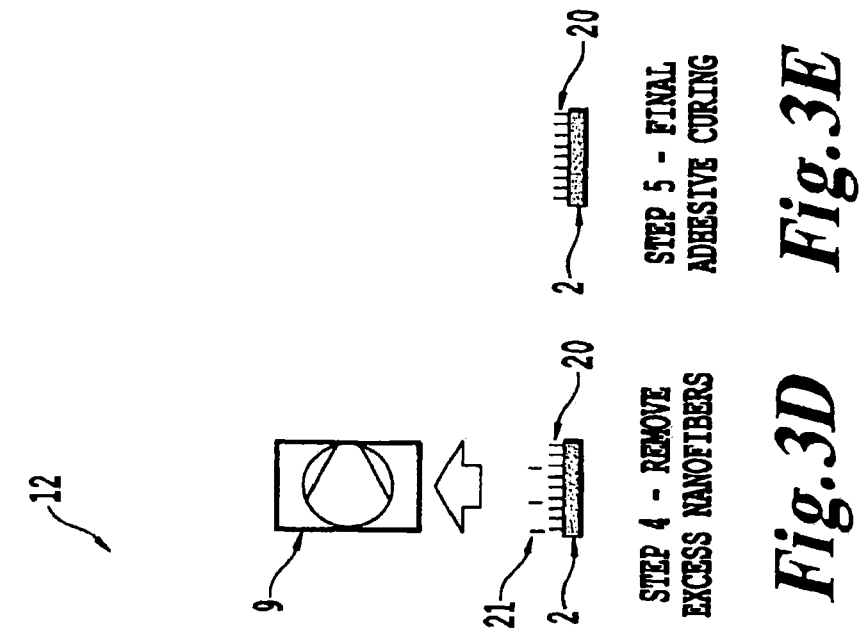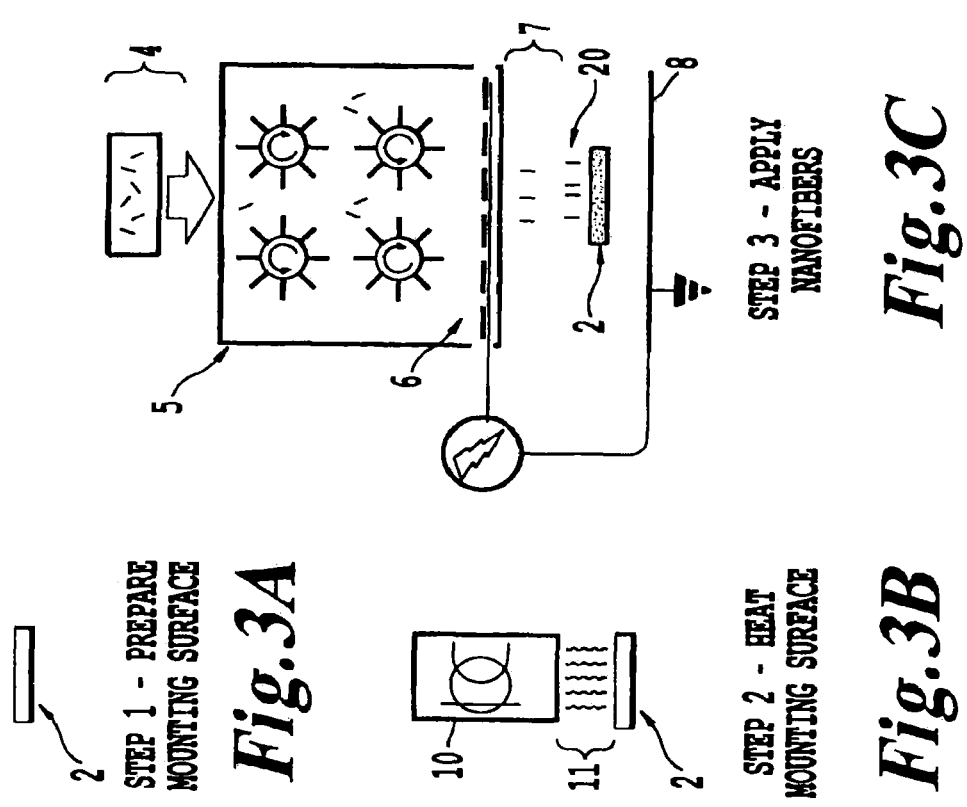

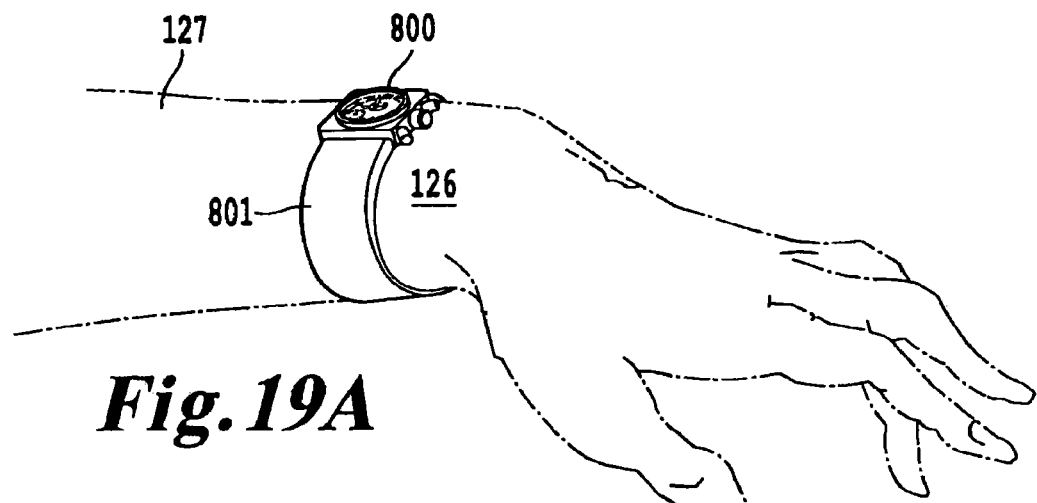
Fig. 19A
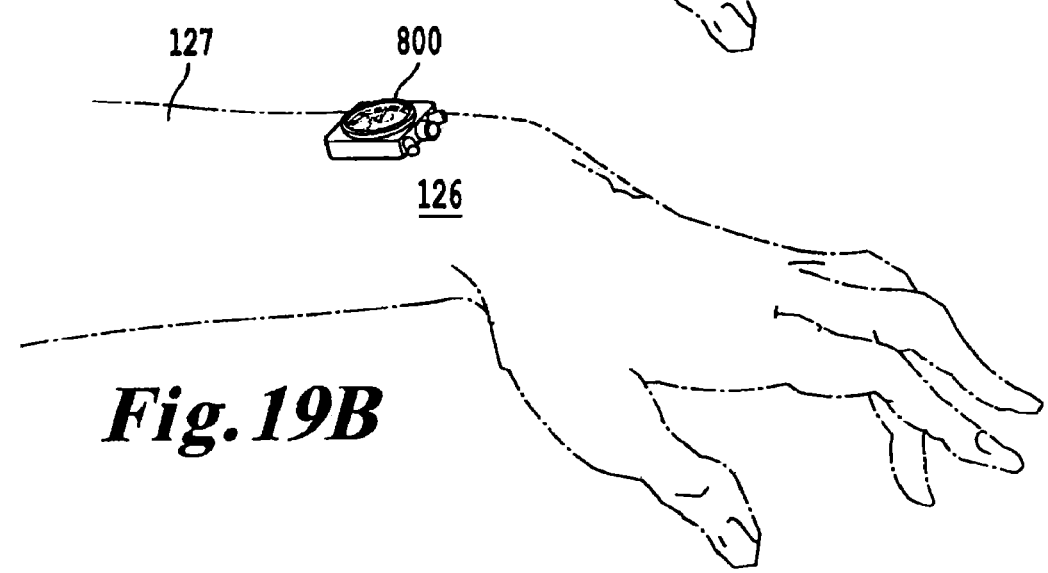
Fig. 19B
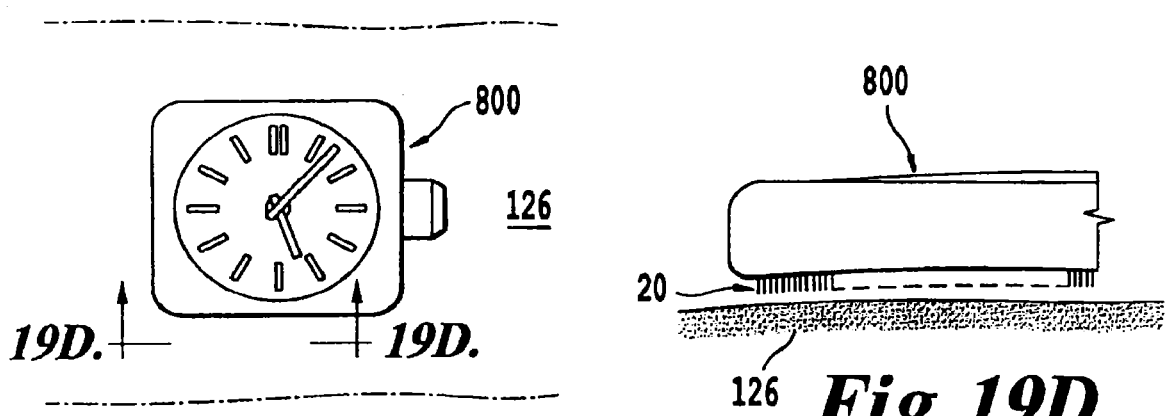
Fig. 19C
Fig. 19D

NANOADHESION STRUCTURES FOR SPORTING GEAR

CROSS-REFERENCE TO RELATED APPLICATIONS

This application is a continuation of U.S. application Ser. No. 13/614,474, filed on Sep. 13, 2012, entitled "Nanoadhesion Structures for Sporting Gear," which is a divisional of U.S. application Ser. No. 12/819,378, filed on Jun. 21, 2010 and issued as U.S. Pat. No. 8,424,474, entitled "Nanoadhesion Structures for Sporting Gear," which is based upon and claims priority under 35 U.S.C. § 119(e) to U.S. Provisional Application No. 61/218,735, filed on Jun. 19, 2009. The entire contents of each of these disclosures are incorporated herein by reference.

BACKGROUND OF THE INVENTION

Field of the Invention

This invention relates to sporting gear having at least one surface equipped for nanoadhesion, more specifically to swimming goggles having a nanofiber surface to attach to the user's body, a shoe having a nanofiber surface on an outsole to attach to a nanofiber surface on a midsole, a nanoadhesive seam to connect panels as part of athletic apparel, and a nanofiber zipper.

Description of the Related Art

Today's sporting gear, including sporting apparel and sporting equipment, may be a combination of the latest innovations of technology from various scientific disciplines. The resulting products are a system of innovative advances all contributing to the performance, safety, and comfort of the athlete. One significant area to improve sporting gear is to attach different sporting gear components together or attach components to the wearer's body. Traditional processes to adhere components to each other and to the user have been imperfect.

In the case of swimming goggles and scuba masks, suction and compression have been traditional approaches to adhere a mask to the user's upper face. However, swim goggles utilizing these approaches frequently leak water into a space between a goggle lens and user's eye causing the user to lose the ability to properly see out of that eye resulting in a loss of potential performance. The swim goggle user may tighten the goggles and thereby push the goggles further into the skin around the eyes in an effort to create a more durable watertight seal. Unfortunately there are negative consequences to tightening goggles because they frequently create red rings around the user's eyes and cause swelling in this skin area by limiting blood flow and lymphatic return.

In the case of shoes, traditional chemical-based adhesives such as epoxy cement have permanently attached outsoles to lower midsoles. For users requiring new outsoles to repair those that have been worn down after miles of use, the practical solution has been to replace the whole shoes.

In the case of athletic seams used in clothing, there is a need for a better technique to bind clothing together at a seam to supplement or replace mere thread. After repeated uses of an article of clothing in athletic events or practice events the thread used for seams may break or tear the adjacent clothing to cause the clothing to become unusable.

In the case of zippers, there is a need for a better zipper. Metal zippers can tear at fabric and plastic zippers may mechanically jam and not allow either opening and/or closing. Further, zipper alternatives provide significant disadvantages. For example, hook and loop fasteners may attach to the wrong surface and cause surface damage.

There has been previous attempts to create goggles having no leaks, shoes having replaceable outsoles, and apparel having more robust seams and zippers. Yet these efforts have produced sporting gear that suffers from either deficiencies in performance, comfort, or safety.

There are adhesive systems in nature that have not been applied to sporting gear. For example, the adhesive system on the feet of some insects and lizards, such as Geckos, Anolis lizards, and skinks has attracted research interest. These organisms have been able to attach and detach their feet to climb smooth surfaces such as glass. The adhesion system involves the use of tiny slender natural protrusions known as setae (singular "seta") attached to their feet. For example, a Tokay gecko lizard possesses seta having a diameter of five microns and a height of 110 microns. The seta may include a set of sub-protrusions which contact other surfaces and have even smaller dimensions. As these organisms climb up smooth surfaces such as glass, the setae help geckos form a temporary attachment so they do not slip and fall. Although aspects of a gecko-like adhesive system have been observed in nature, the technology has not yet been successfully applied to commercial products.

Although foregoing research efforts have met with varying degrees of success, there remains an unresolved commercial need for more leak-proof swimming goggles, shoes with replaceable soles, and athletic apparel with more robust seams and zippers.

SUMMARY OF THE INVENTION

One aspect of the present invention may be to address and resolve the above limitations of conventional sporting gear.

A man-made adhesive mechanism may be customized as part of sporting gear having a mounting surface that may be attached to a second surface. The adhesive mechanism may include a first plurality of nanofibers attached to the mounting surface. The first end of each nanofiber may be attached to the mounting surface using a flocking process along with the application of either thermal or radio frequency bonding. The second end of each of the first plurality of nanofibers may be placed in contact with the second surface not having nanofibers or a plurality of second nanofibers attached to the second surface to form a temporary attachment called nanoadhesion which may include a van der Waals force contribution.

The nanoadhesion attachment may be detached by pulling the first plurality of nanofibers away at an angle from the second surface. Each nanofiber may include a fiber shaft less than 100 microns in length with a diameter of less than half a micron.

In a first aspect, the present invention may be adapted to attach swimming goggles to the wearer's face. Goggles may include a lens component, also known as a lens cup, for each eye. A lens component may have a lens surface and a mounting surface. The mounting surface may be configured to form a seal with the skin around a wearer's eye. The mounting surface may be made of the same material as the lens surface or the mounting surface may be included as part of a lower modulus of elasticity material attached as part of the lens component.

Nanofibers are attached to goggles at the mounting surfaces of each lens component and form a protrusion emanating from the mounting surface that contacts the skin around the wearer's eyes. The nanofibers may be attached around the entire perimeter or only in areas of the mounting surface that are prone to separate from the skin during use of the swimming goggles (such as to the right and left of the eye). The nanofibers may provide a nanoadhesion force to better keep the mounting surface attached to the skin during use and may easily be detached from the skin at the end of use by pulling the mounting surface away from the skin.

In a second aspect, the present invention may be adapted to attach and detach components of an athletic shoe having an outsole, midsole assembly, and upper. The outsole contains a bottom surface to contact the ground and a top surface to contact the midsole assembly. The top surface of the outsole contains a first mounting surface with a first set of nanofibers attached. The midsole assembly may contain several components to provide shock absorption and stability such as a rear lower midsole, a directional cradle, and a primary midsole. A bottom surface of the midsole assembly may contain a second mounting surface having a second set of nanofibers attached. The outsole may be attached to the midsole assembly by bringing the first and second set of nanofibers together.

Other sets of nanofibers and mounting surfaces may be included to attach the midsole assembly to the upper and/or the midsole components together. The attachment process allows worn components to be replaced and different components to be swapped out to provide several different shoe configurations for the same upper. The attachment process also improves manufacturing efficiency.

The shoe assembly may include sunken surfaces and complementary three-dimensional shapes to define the mounting surfaces and to thereby assist in a mechanical interference to keep the outsole in place while the shoe may be used. Further the shoe may include seals and/or gaskets to keep contaminants such as dirt or water away from nanofibers.

In yet a third aspect, the present invention may be adapted to create a nanofiber seam to attach woven panels to form various athletic gear such as shirts, jackets, shorts, pants, hats, socks, and/or shoes. Nanofibers may also be used to create attachments between garments, for example from a glove to a jacket or a coat to a pant, or a pant to a boot.

An apparel item may be made up of various components (herein "panels") that are attached at one or more seams. The panels are cut to the proper size. Panels may have nanofibers attached via the flocking process along an edge of each panel where a seam may be intended to join the panels. The nanofibers may be attached to one side or both sides of each of the edges. The panels are then attached by bringing the nanofibers in contact. The panels may also be folded over to allow additional nanofibers to come into contact and to be attached together. The nanofibers may be pulled apart to allow the panels to be orientated in a different position to each other. The seam may be supplemented by thread for strength.

In yet a fourth aspect, the invention may be adapted to create a nanofiber-based zipper for athletic gear such as apparel, gym bags, footwear, and the like that contain panels as described above. The nanofiber zipper may be used to attach a first edge of a first panel with a second edge of a second panel. The first and second panels may have nanofibers attached via the flocking process along an edge of each panel where the nanofiber zipper may be intended to attach the panels. The nanofibers may be attached to one side of the first panel edge and to one side of the second panel edge. The panels are then attached by bringing the nanofibers in contact. The user may unzipper the nanofiber zipper by pulling the nanofibers apart at an angle through the use of a zipper slider that may be outfitted with a control handle. The nanofiber zipper may be supplemented by other fasteners such as traditional hooks or buttons.

As should be apparent, the invention can provide a number of advantageous features and benefits. It is to be understood that, in practicing the invention, an embodiment can be constructed to include one or more features or benefits of embodiments disclosed herein, but not others. Accordingly, it is to be understood that the preferred embodiments discussed herein are provided as examples and are not to be construed as limiting, particularly since embodiments can be formed to practice the invention that do not include each of the features of the disclosed examples.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

The invention will be better understood from reading the description which follows and from examining the accompanying figures. These are provided solely as non-limiting examples of the invention. In the drawings:

FIGS. 2A-2E illustrate a process to attach the nanofiber to a mounting surface using an adhesive according to an embodiment of the present invention;

FIGS. 3A-3E illustrate a process to attach the nanofiber to a mounting surface using heat or high frequency radio waves according to an embodiment of the present invention;

FIG. 19A illustrates a nanofiber watch attached to a wrist using a strap as viewed from the side;

FIG. 19B illustrates the nanofiber watch attached to a wrist without the strap as viewed from the side;

FIG. 19C illustrates the nanofiber watch attached to a wrist without the strap as viewed from the top;

FIG. 19D illustrates the nanofiber watch with nanofibers attached and the wrist as viewed from the side;

DETAILED DESCRIPTION OF THE PREFERRED EMBODIMENTS

Figure 1:
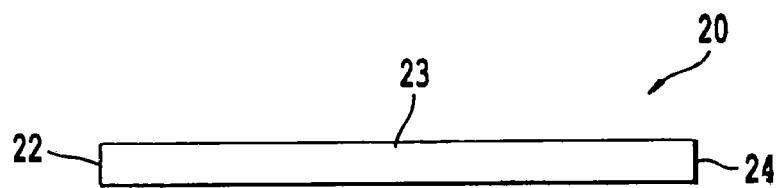
FIG. 1 illustrates a nanofiber according to an embodiment of the present invention.

Referring now to the drawings, wherein like reference numerals designate identical or corresponding parts throughout the several views.

Reference will now be made in detail to the present preferred embodiments of the invention, examples of which are illustrated in the accompanying drawings. Wherever possible, the same reference characters will be used throughout the drawings to refer to the same or like parts.

FIG. 1 illustrates an adhesive protrusion hereafter known as a nanofiber preferably having a length from 5 to 100 microns in length. The nanofiber diameter may be preferably 0.05 times its length which may range from 250 nanometers to a micron. A first terminal end 22 of a nanofiber shaft 23 may not be attached to a mounting surface. The opposite terminal end 24 of the nanofiber shaft may be attached to a mounting surface via an adhesive or other attachment method such as thermal or high frequency radiation induced bonding or the like.

When the first terminal end 22 of the nanofiber 20 contacts another surface, attraction forces, including van der Waal forces, adhere the nanofiber end 22 to the other surface. The other surface may also have a second nanofiber attached by adhesive that adheres to the nanofiber and/or the mounting surface. The attraction forces produced by contact with the nanofiber is referred here as nanoadhesion. The resulting attraction forces mimic the action of setae on a gecko's foot.

The nanofibers are constructed using various methods. These methods generally involve casting or molding the fibers, growing them in a solution, or deposition. One method may be to use lithography methods where a recess may be etched in a semiconductor substrate and nitride and oxide layers are deposited on the substrate. The surface then may be patterned and etched. When the underlying structure is etched, a stress difference between the oxide and nitride layers causes the structure to curl and to form a shaft structure. The ends 22 of the shaft may be roughened to increase surface area available for contact by using wet etching, radiation, plasma roughening, electrochemical etching and others.

A preferred method of making nanofibers involves creating yarns of sub-micron diameter fibers. These yarns may be cut from the yarns to release the fibers in lengths such that when adhered to a mounting surface, in a position perpendicular to the mounting surface, the nanofiber will not collapse under its own weight.

The nanofibers may be then collected and prepared for attachment to the mounting surface. The nanofibers may be cleaned to remove contaminants and then chemically treated to accept an electric charge. The nanofibers may be spin-dried and then oven-dried to a specific moisture content. Conductivity may depend on moisture content, so it may be preferable that some moisture remain with the nanofibers. The nanofibers 20 are then packaged in moisture-proof containers 4 to maintain optimal moisture until a later attachment of the nanofibers 20 to a mounting surface.

The nanofibers 20 may then be attached to a mounting surface via a flocking process. There are various types of flocking methods available, but an electrostatic-based flocking method may be preferred for attaching nanofibers to a mounting surface because of its ability to better align the nanofibers to the mounting surface.

Two electrostatic-based flocking processes are preferred for permanently attaching the nanofibers 20 to the mounting surface. The first process involves an adhesive to attach the nanofibers 20 to the mounting surface and the second process involves heat instead of the adhesive.

In the first process shown in FIGS. 2A to 2E, the flocking process begins by applying a chemically-compatible adhesive to the mounting surface which has been properly cleaned. In the case of a textured mounting surface having peaks and valleys, the adhesive may only be applied to the peaks. Various adhesives may be used such as: a low viscosity ultra-violet cure epoxy, uncured silicone rubber, polyurethane resin, plastisol (polyvinyl chloride particles suspended in a plasticizer), or the like.

As shown in FIG. 2B, the adhesive may be applied to the mounting surface in the area(s) where the nanofibers 20 are desired to be attached. The adhesive thickness applied may be dependent upon the adhesive used and the mounting surface. A statistical process control methodology may begin with a preferred adhesive thickness that may be approximately ten times the shaft diameter of the nanofiber. The thickness may then be adjusted to optimize the reliability of the adhesive to hold the nanofiber and the efficacy of the final product.

This methodology will create a scaled fiber assembly substantially similar to that encountered in nature within the gecko's foot, and in a manner that lends itself to large scale industrial production.

After the adhesive 3 may be applied, the mounting surface 2 may be placed between the flock hopper 5 and a grounded electrode 8 as shown in FIG. 2C. The flock hopper 5 may be filled with the many nanofibers transferred from the moisture-proof containers 4. The flock hopper 5 may have rotating flock stirrers with a plurality of arms configured to allow the nanofibers 20 to become airborne randomly to produce a uniform pattern at the exit of the hopper. The airborne nanofibers may then pass through an electrode grid 6 at the exit of the flock hopper which imparts a charge on the airborne nanofibers 20 that is an opposite electric charge compared to the grounded electrode 8.

The temperature and humidity of the flocking environment may be critical in controlling the charge on the airborne nanofibers. Humidity too low may cause the nanofibers to not effectively take on an electrical charge and humidity too high may cause the nanofibers to undesirably stick or clump to each other. These humidity and temperature levels may be optimized according to the nanofiber characteristics and the adhesive used.

Once the nanofibers 20 are electrically-charged and released from the flock hopper 5 to be airborne above the mounting surface as elements 7, the nanofibers 7 will align themselves with the magnetic field between the electrodes 6, 8 and accelerate towards an oppositely-charged electrode 8 arranged below the mounting surface 2. The aligned and accelerated nanofibers 7 collide with and embed into the adhesive 3 in a position substantially perpendicular to the mounting surface 2.

Alternatively, the adhesive may be electrically charged instead of having a grounded electrode beneath the mounting surface. The nanofibers 20 would similarly embed into the adhesive 3 in the position substantially perpendicular to the mounting surface 2.

As shown in FIG. 2D, the mounting surface 2 may then be removed from between the flock hopper 5 area and excess nanofibers 21 which are not embedded into the adhesive 3 may be removed via vacuum 9 or other suction device. The adhesive 3 may be allowed to cure and the nanofibers 20 remain attached and generally perpendicular to the mounting surface as shown in FIG. 2E.

The second process may be shown in FIGS. 3A to 3E. The nanofibers 20 used in this process may be made of thermoplastic which may form a bond with the mounting surface 2 greater than a certain temperature. Various thermoplastics may be used such as Poly(methyl methacrylate) or PMMA, polyethylene (PE), Polystyrene (PS), or the like.

As represented in FIG. 3A, the mounting surface 2 may first be prepared for the attachment of the nanofibers 20 by cleaning using surfactants or other cleaning agents available to remove contaminants that may inhibit the subsequent process steps. Next, as shown in FIG. 3B, the mounting surface 2 may be heated. The heater 10 may be an oven, a frequency radiation emitter, or the like. The heater 10 may use heating means 11 such as radiation heat transfer or convention heat transfer to heat the mounting surface 2 to a temperature above the melting point of the material used to make the nanofibers 20. For example, the melting point of PMMA is approximately 135 degrees Celsius, polyethylene is between 105 to 130 degrees Celsius, and polystyrene melts at roughly 240 degrees Celsius.

After heating, the mounting surface 2 may be placed between the flock hopper 5 and a grounded electrode 8 as shown in FIG. 3C. The flock hopper 5 may be filled with the many nanofibers transferred from the moisture-proof containers 4. The flock hopper 5 converts the nanofibers 20 into airborne nanofibers 7 which then pass through an electrode grid 6 at the exit of the flock hopper to impart a charge on the airborne nanofibers 20 that is an opposite electrical charge compared to that of the grounded electrode 8.

Once the airborne nanofibers 7 are electrically-charged and released from the flock hopper 5 to be airborne above the mounting surface, they will align themselves with the magnetic field between the electrodes 6,8 and accelerate towards an oppositely-charged electrode 8 arranged below the substrate 2. The aligned and accelerated nanofibers 7 collide with the heated mounting surface 2 and nanofibers 7 partially melt at the contact point between the nanofibers 20 and the heated mounting surface 2 to form a permanent attachment point.

The mounting surface 2 may then be removed from between the flock hopper 5 area and the excess nanofibers 21 that are not attached to the mounting surface 2 are removed via vacuum 9 or other suction device as shown in FIG. 3D. The mounting surface 2 may be allowed to cool and the nanofibers 20 remain attached and generally perpendicular to the mounting surface as illustrated in FIG. 3E.

First Embodiment—Nanofiber Swimming Goggles

Sporting gear provides useful applications for nanoadhesion. In the first embodiment, swim goggles are commonly used to enable swimmers to keep water out of their eyes. The swim goggles 101 are illustrated in FIGS. 4A to 7B. The swim goggles 101 may include two eye components 102, a nose bridge 108 and a head band 104. The nose bridge 108 may be designed to hold each of the eye components 102 a fixed distance apart. The head band 104 may fit around the head of the wearer and be attached at each end to the eye components 102. Each eye component 102 may include a lens surface 103, a connector interface 107, a head band interface 105, and a sealant surface 106. The connector interface 107 may connect the nose bridge 108 to the eye component 102. The head band interface 105 may connect the head band 104 to the eye component 102. The sealant surface 106 may contact a skin contact area 123, 124 of the left or right eye 121, 122 as shown in FIG. 8A. The shape of the sealant surface 106 may be similar to the shape of the skin area 123, 124 to allow contact all around the eye 121, 122. The sealant surface 106 may be the same material as the lens surface 103.

Figure 5A:
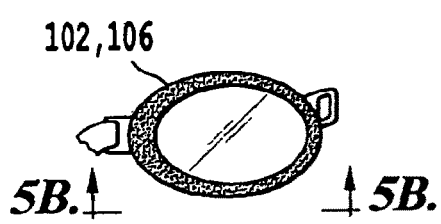
FIG. 5A illustrates the swimming goggle according to an embodiment of the present invention as viewed from the back.
Figure 5B:
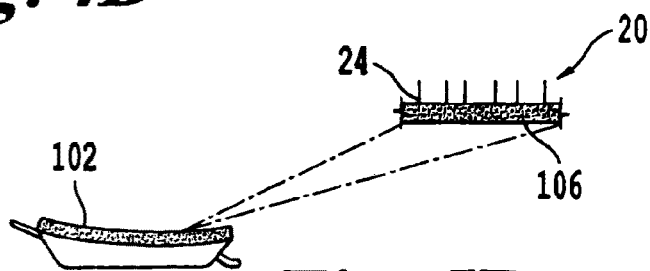
FIG. 5B illustrates the swimming goggle according to an embodiment of the present invention as viewed from the top and including a close-up of nanofibers attached.
Figure 6A:
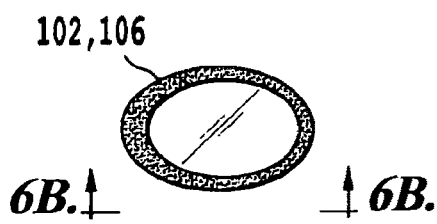
FIG. 6A illustrates a swimming goggle according to an embodiment of the present invention without a head band as viewed from the back.
Figure 6B:
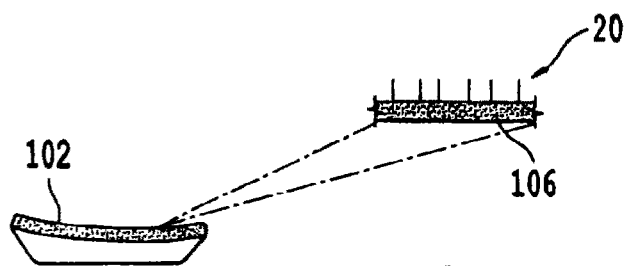
FIG. 6B illustrates the swimming goggle according to an embodiment of the present invention without a head band as viewed from the top and including a close-up of nanofibers attached.

As shown in FIG. 5B, the sealant surface 106 may have many nanofibers 20 attached at the terminal end 24. The unattached terminal ends 22 of the nanofibers 20 are configured to contact the skin contact area 123, 124 when the goggles 101 are worn by a user and thereby form a nanoadhesion attachment with the skin contact area 123,124.

The nanofibers 20 are not configured to penetrate the skin contact area 123 which is composed of several skin layers including the epidermis and dermis. The human epidermis is the outer skin layer and its minimum thickness is 50 microns at the eyelids. The human epidermis has five sub-layers and the cells divide at the inner layers and are gradually pushed to the exterior layers where their cells flatten and die to be shed every two weeks. The nanofibers 20 may be configured to merely contact the outer layers of the epidermis to avoid skin injury.

Another embodiment of the goggles may have a rubber gasket. The rubber gasket may act as the sealant surface 106 and may be merely attached to the eye component 102 via adhesive such as epoxy cement or the like. The gasket 106 may be made from rubber, silicone, or other soft material. One end 24 of each nanofiber 20 may be permanently attached to the rubber gasket 106 using one of the flocking processes 1, 12. The skin contact area 123, 124 contacts the unattached end 22 of the nanofibers 20 when the swim goggles 101 are worn and a nanoadhesion attachment may be made between the nanofiber 20 and the skin contact area 123,124.

Embodiments of the goggles 101 are intended to be used by the wearer in a similar way. The wearer places the eye components 102, 109 over the eyes 121, 122, so that the end 22 of the nanofibers 20 attached to the sealant surface 106 contacts the skin contact area 123. The wearer then fastens the head band 104 around the wearer's head to provide a comfortable fit which pulls the sealant surface 106 against the skin 123 in order to form a watertight seal. The wearer may also slightly depress the eye component 102 against the skin 123 to force a small amount of air to be pushed out from between the eye compartment 102 and the eye 121. When this air is pushed out, the watertight seal keeps the air from returning and thereby maintains a negative suction between the eye component 102 and the corresponding eye 121 to improve the watertight seal. The negative suction is an absolute pressure less than ambient pressure. The user may also depress the eye component 109 to achieve a similar negative suction to improve the watertight seal related to the other eye 122.

As the wearer engages in a water activity involving immersing the user's head and swim goggles 101 in water, the watertight seal may be maintained because the skin 123 remains in contact with the sealant surface 106 as a result of the negative suction, the pull of the head band 104, and the nanoadhesion attraction between the nanofibers 20 and the skin 123. This watertight seal may be more robust than goggles without nanofibers 20, because as the wearer engages in vigorous activities while wearing the goggles 101 the tight seal may be vulnerable to compromise as the contact skin area 123 changes shape relative to the sealant surface 106 during the water activity.

When the water activity has been completed, the wearer merely releases the head band 104 from the back of the wearer's head and the wearer pulls the eye components 102, 109 from the skin contact areas 123, 124.

A second aspect to this first embodiment may be swim goggles without a head band 104, connector interface 107, and nose bridge 108 as shown in FIGS. 5A and 5B. In this second aspect, each eye component 102 is identical to each other and has nanofibers 20 attached to the sealant surface 106. Just prior to the wearer engaging in a water activity involving immersing the user's head and swim goggles in water, an eye component is placed in contact with each of the respective skin areas 123, 124 so that the nanofibers 20 are in contact with the respective skin areas 123, 124. A watertight seal may be maintained as described with respect to a single eye component because the skin 123 remains in contact with the sealant surface 106 as a result of negative suction and the nanoadhesion attraction between the nanofibers 20 and the skin 123. When the water activity has been completed, the wearer merely pulls each eye component from the respective skin areas 123, 124.

Figure 7A:
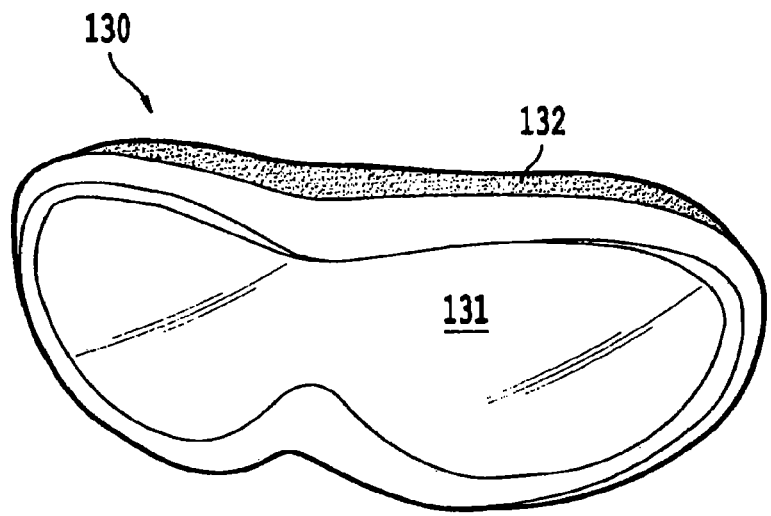
FIG. 7A illustrates a ski goggle according to an embodiment of the present invention without a head band as viewed from the front.
Figure 7B:
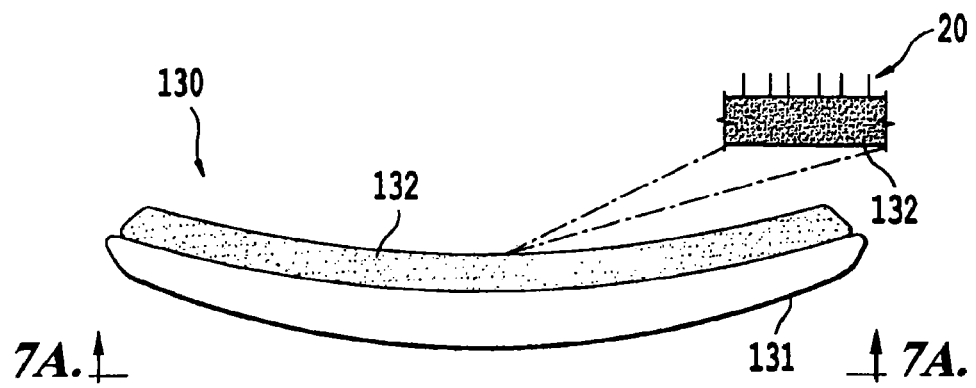
FIG. 7B illustrates the ski goggle according to an embodiment of the present invention without a head band as viewed from the top and including a close-up of nanofibers attached.
Figure 8A:
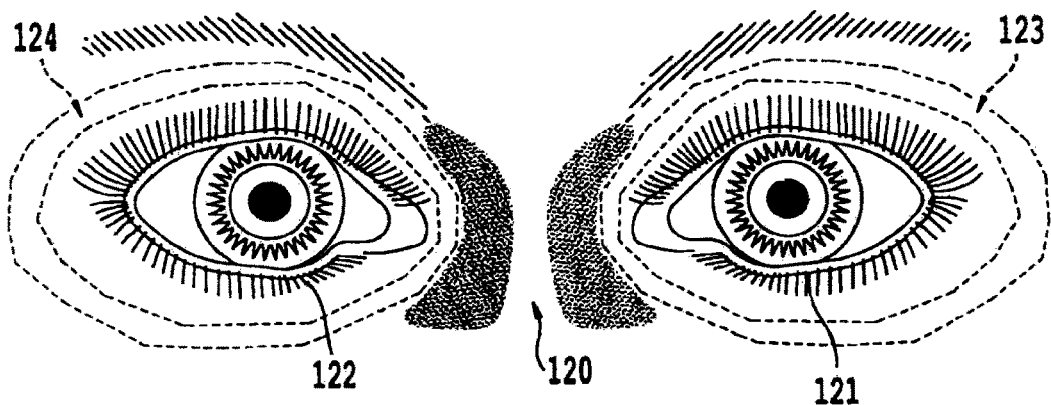
FIG. 8A illustrates a set of skin areas or regions designed to be in contact with the swimming goggles according to an embodiment of the present invention as viewed from the front.
Figure 8B:
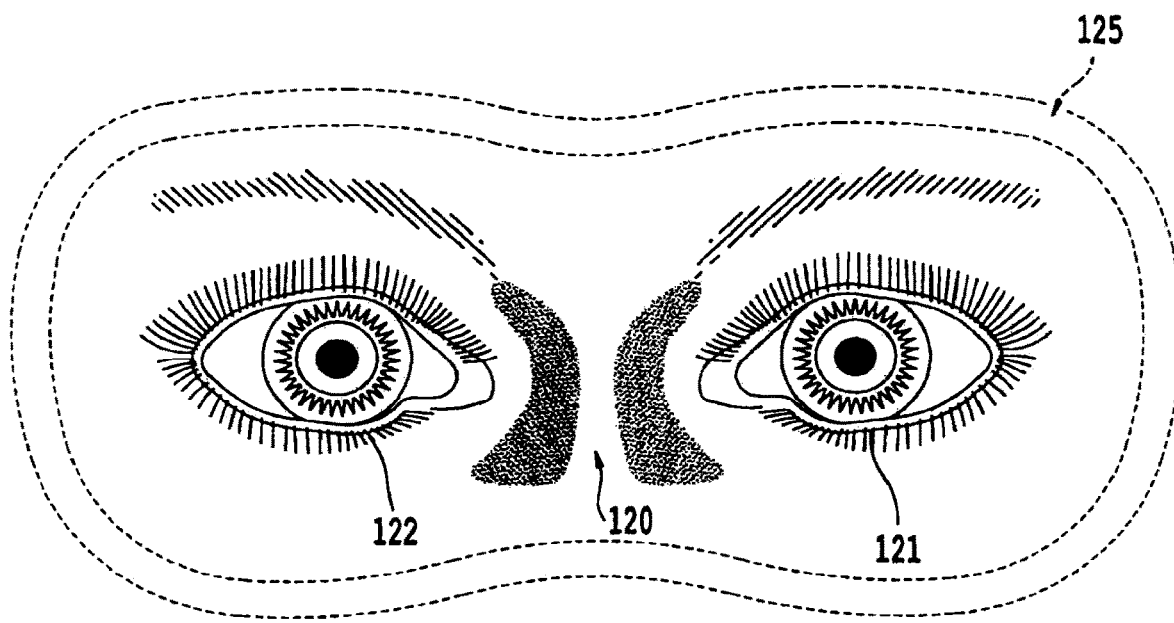
FIG. 8B illustrates a skin area or region designed to be in contact with the ski goggle according to an embodiment of the present invention as viewed from the front.

As shown in FIGS. 7A and 7B, ski goggles may be a second aspect of this first embodiment. The ski goggles 130 may include a lens 131 and a sealant surface 132. The ski goggles 130 may or may not also include a strap (strap not shown). The sealant surface 132 has nanofibers 20 attached using at least one of the flocking processes mentioned earlier. Just prior to the wearer engaging in a skiing activity, the nanofibers 20 are placed in contact with a skin area 125 as shown in FIG. 8B. A nanoadhesion attraction between the skin area 125 and the nanofibers 20 is created which keeps the ski goggles 130 attached to the skin area 125. When the skiing activity has been completed, the wearer merely pulls the sealant surface 132 away from the skin area 125. Other sports goggles, prescription or non-prescription, are also embodied in this application and can be similarly constructed.

In yet another embodiment, the sealant surface 132 having nanofibers 20 may be located instead on a waistband or shirt cuff to grip the nearby skin better.

Second Embodiment—Replaceable Shoe Components

Figure 9:
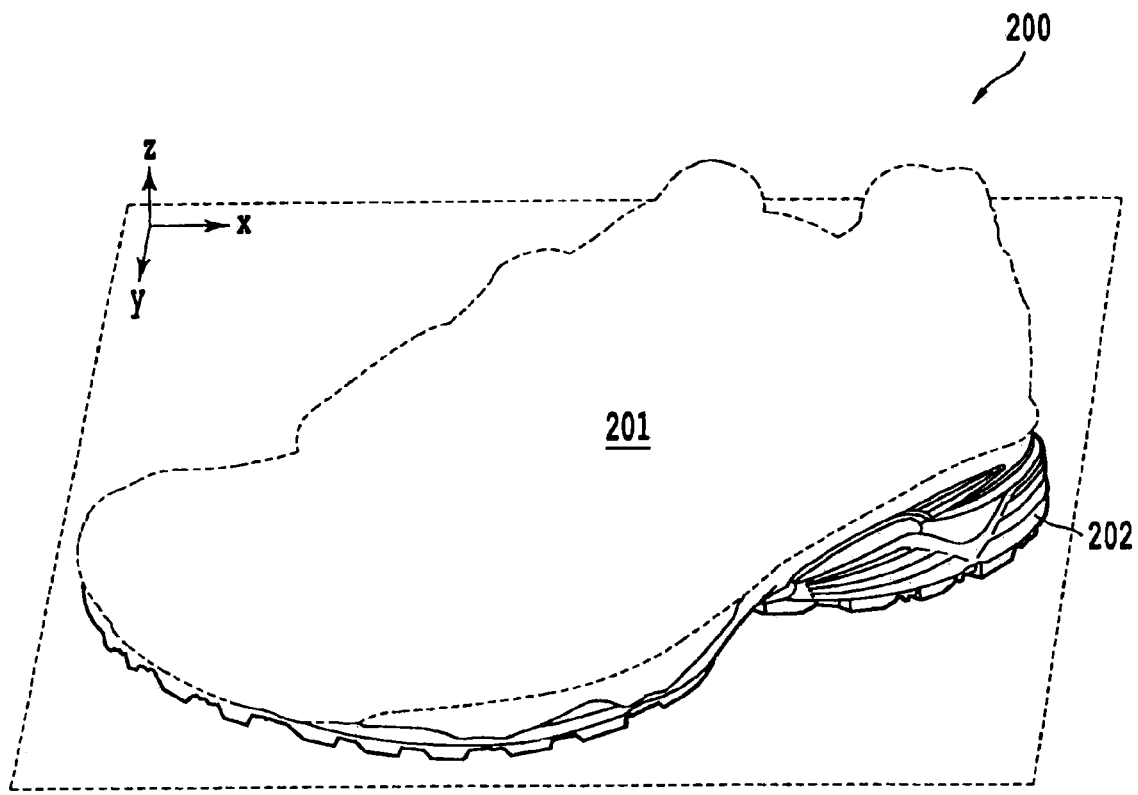
FIG. 9 illustrates a shoe having components attached by nanofibers according to an embodiment of the present invention as viewed from the side.
Figure 4A:
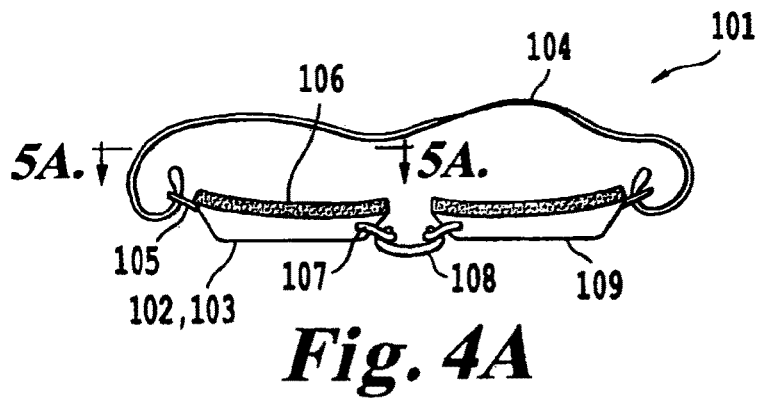
FIG. 4A illustrates a pair of swimming goggles according to an embodiment of the present invention as viewed from the top.
Figure 4B:
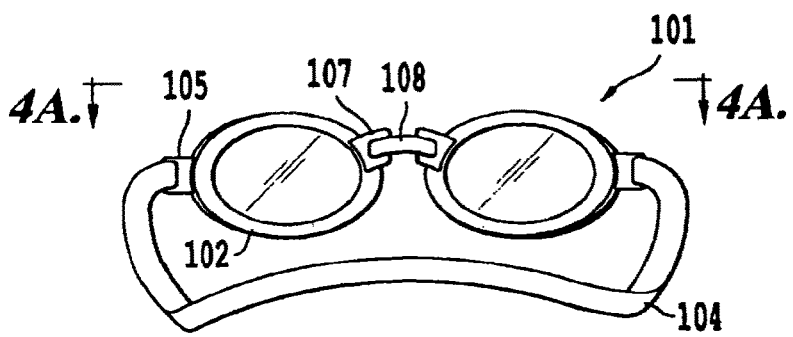
FIG. 4B illustrates the pair of swimming goggles according to an embodiment of the present invention as viewed from the front.
Figure 10:
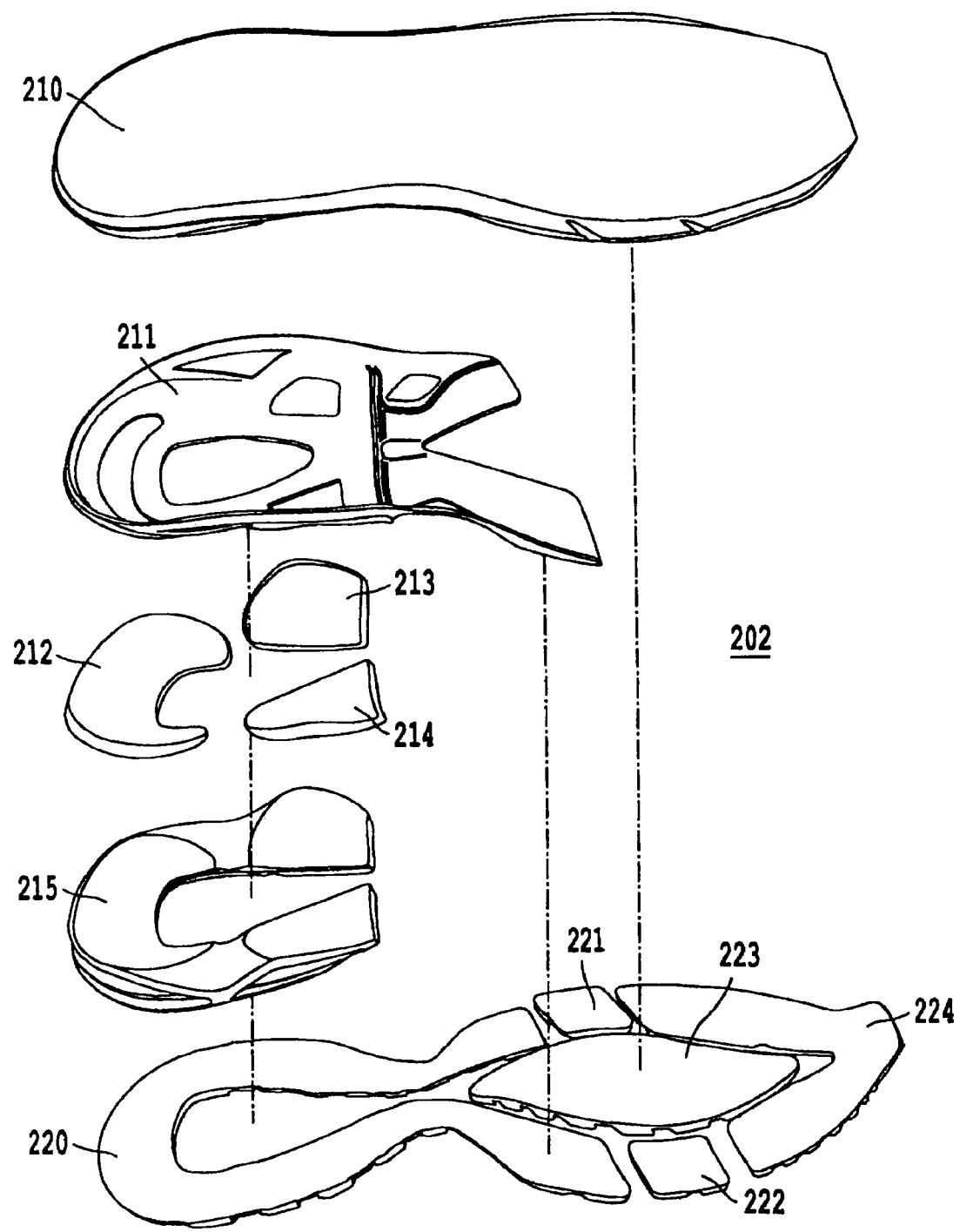
FIG. 10 illustrates a lower from the shoe having components attached by nanofibers according to an embodiment of the present invention as viewed from the upper side.
Figure 11:
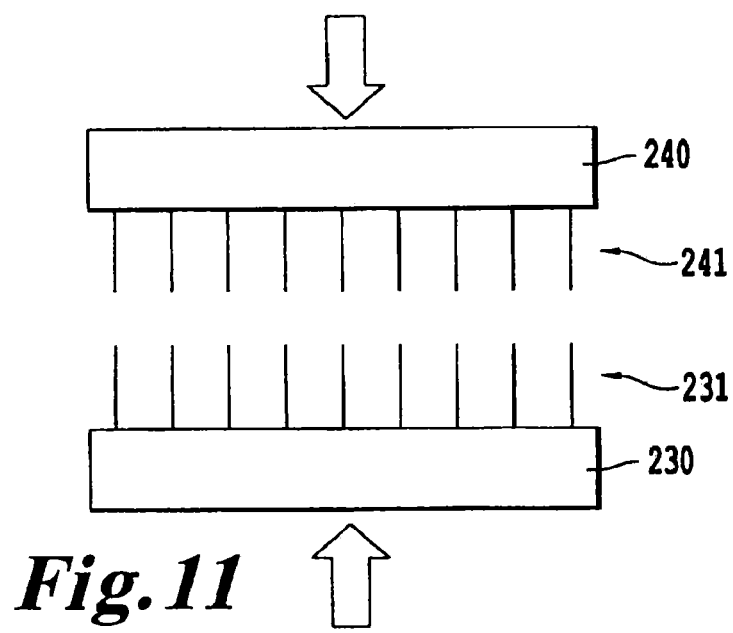
FIG. 11 illustrates a pair of mounting surfaces being attached by nanofibers connected to each of the mounting surfaces according to an embodiment of the present invention as viewed from the side.

Another embodiment utilizing the nanofibers 20 is illustrated in FIG. 9 as an athletic shoe 200 having an upper 201 and a lower 202. FIG. 10 shows the lower 202 for a left foot, but the right shoe has a similar construction. The lower 202 may include a full-length primary midsole 210, a directional cradle 211, a first cushion 212, a second cushion 213, a third cushion 214, a rear lower midsole 215, a rear outsole 220, a lateral outsole 221, a medial outsole 222, a center outsole 223, and a front outsole 224. The directional cradle 211 may be attached to the primary midsole 210. The cushions 212, 213, 214 may be attached to both the directional cradle 211 and the rear lower midsole 215. The components of the outsole 220, 221, 222, 223, 224 may be attached to the rear lower midsole 215, directional cradle 211, and/or primary midsole 210. Any of the components that are part of the lower 202 may be attached together where as shown in FIG. 11 a first set of nanofibers 241 are permanently attached to first mounting surface 240 and a second set of nanofibers 231 are permanently attached to a second mounting surface 230 via the flocking processes 1, 12. The mounting surfaces 230,240 may be part of the components of the lower 202. Then, using the process of nanoadhesion, the first and second nanofibers 231, 241 are placed in contact as the components of the lower 202 are placed in contact to form a nanoadhesion attachment. The attachment may be temporary because the user may pull the lower components (elements 210-215 and/or 220 to 224) apart to remove or replace the component with a second component.

The nanoadhesion embodiments of shoe 200 are intended to be used by the wearer in a similar way. The wearer inserts her foot into the upper 201 and fastens the upper 201 comfortably to the foot so the foot may be disposed between the upper 201 and the lower 202. The wearer may engage in whatever activity desired so that the outsole components 220, 221, 222, 223, 224 may have a set of impacts with the ground.

When the activity has been completed, the upper 201 may be unfastened and the wearer's foot removed from the shoe 200. When one or more of the components of the lower 202 become worn beyond repair and need to be replaced, then the wearer will pull the set of nanofibers 231 permanently attached to the worn component from the set of nanofibers 241 attached to another component. Next, the wearer may attach a replacement component having a new set of nanofibers 231 on a mounting surface 230 to the old corresponding set of nanofibers 241 on the other component by bringing them in contact.

Third Embodiment—Nanofiber Seams

Figure 12:
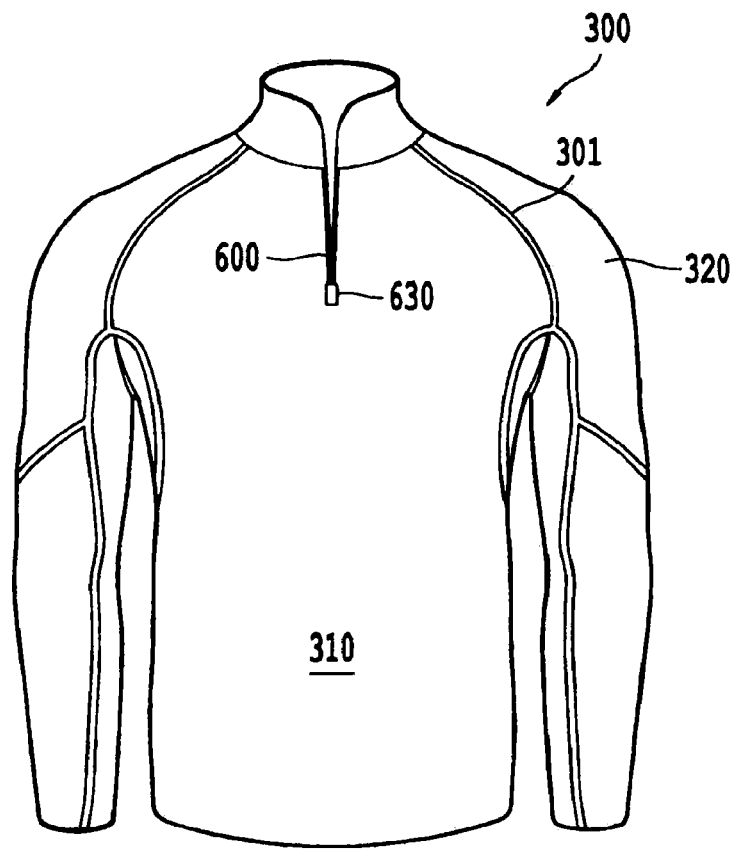
FIG. 12 illustrates an athletic garment having a seam and a zipper utilizing nanofibers according to an embodiment of the present invention as viewed from the front.

Yet another embodiment may be to produce a nanofiber seam to connect woven panels as part of athletic gear such as shirts, jackets, shorts, pants, hats, socks, and/or shoes. Various seam configurations may be created with nanofibers. For example, FIG. 12 illustrates an athletic shirt 300 having a first woven panel 310 and a second woven panel 320 attached by a nanofiber seam 301.

Figure 13A:
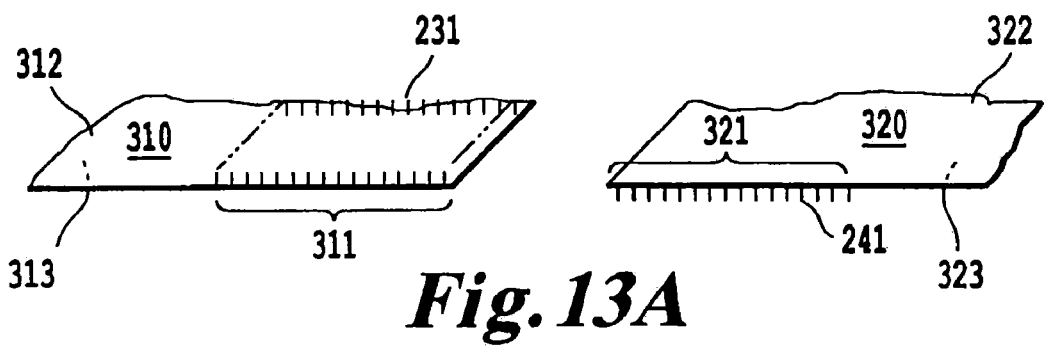
FIG. 13A illustrates a set of two apparel panels having nanofibers prior to attachment according to an embodiment of the present invention as viewed from the side.
Figure 13B:
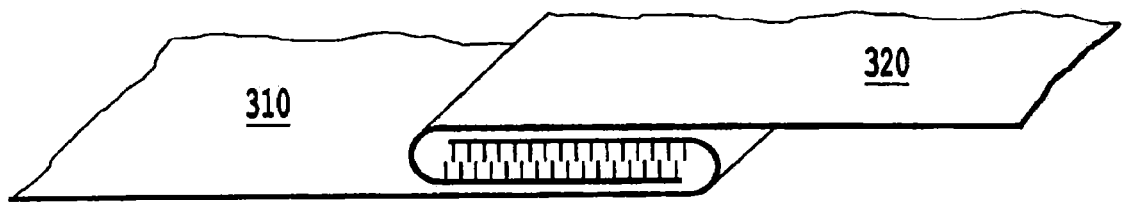
FIG. 13B illustrates the set of two apparel panels having nanofibers attached and folded according to an embodiment of the present invention as viewed from the side.
Figure 13C:
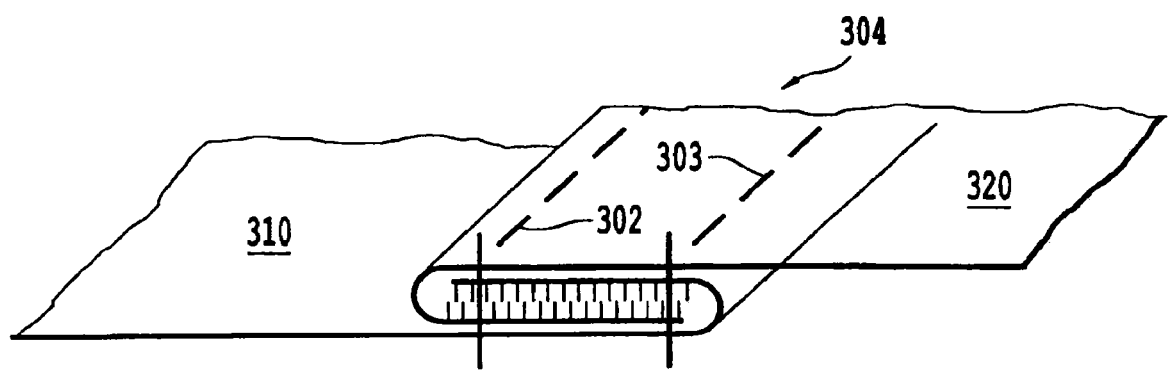
FIG. 13C illustrates the set of two apparel panels having nanofibers attached, folded, and double-stitched with thread according to an embodiment of the present invention as viewed from the side.

The woven panels 310, 320 may first be cut to the proper size prior to being attached by the seam 301. The woven panel 310 has a top side 312 and a bottom side 313 as shown in FIG. 13A. The woven panel 320 has a top side 322 and a bottom side 323. The panels 310, 320 may have nanofibers 231, 241 attached via the flocking process 1, 12 along an edge of each panel where a seam may be intended to join the panels. The nanofibers 231 may be attached to one side of the panel 310 at a panel edge 311 as shown by FIG. 13A. The nanofibers 241 may be permanently attached to one side of the panel 320 at a panel edge 321 using the flocking process 1, 12. The panels 310, 320 are then attached by bringing the nanofibers 231, 241 in contact at the panel edges 311, 321. FIG. 13B shows the attached panel edges 311, 321 after being folded over. FIG. 13C shows thread stitches 302, 303 added to add strength and to form a nanofiber seam 304. Prior to the stitching 302, 303 being applied, the nanofibers 231,241 may be pulled apart to allow the panels 310, 320 to be reattached in case they have been incorrectly positioned together the first time.

Figure 14A:
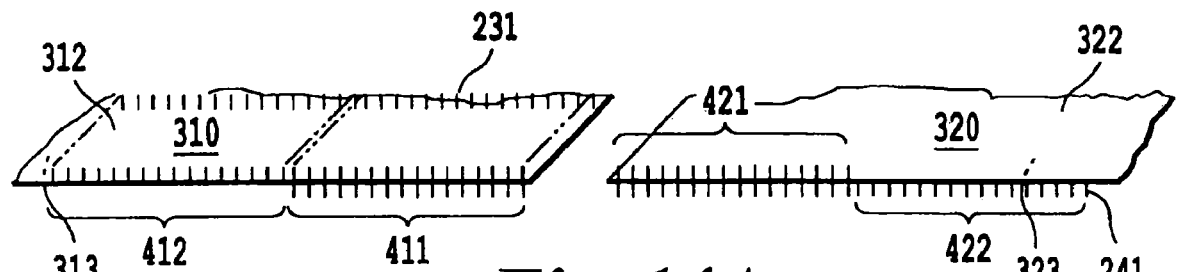
FIG. 14A illustrates a set of two apparel panels having double-sided and single-sided nanofibers prior to attachment according to an embodiment of the present invention as viewed from the side.
Figure 14B:
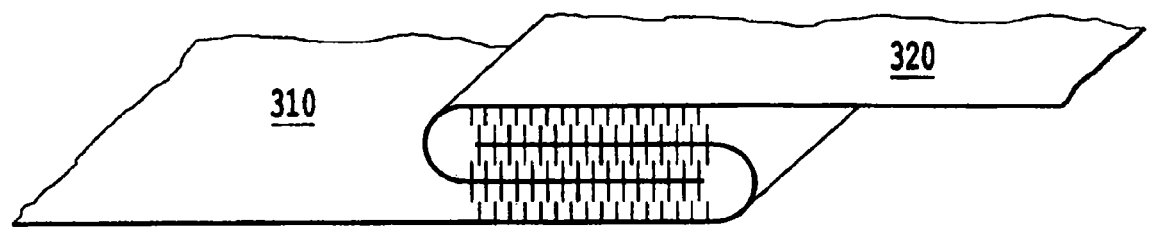
FIG. 14B illustrates the set of two apparel panels having double-sided and single-sided nanofibers attached according to an embodiment of the present invention as viewed from the side.
Figure 14C:
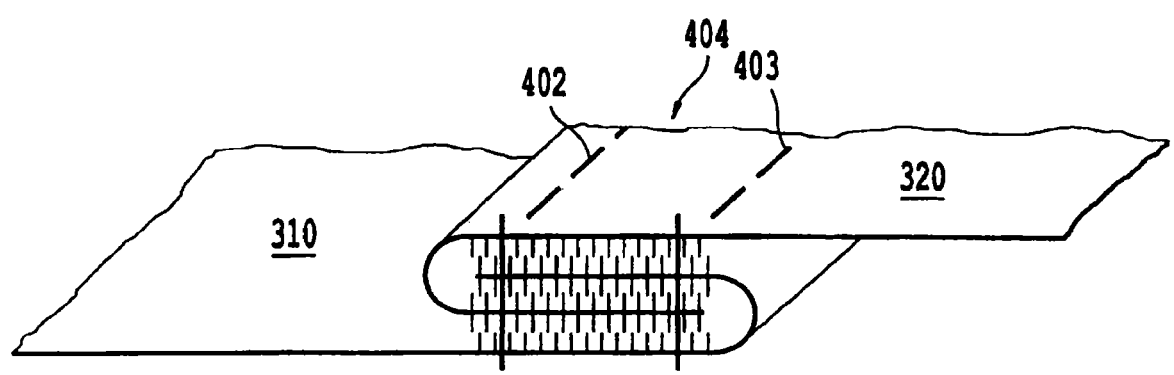
FIG. 14C illustrates the set of two apparel panels having double-sided and single-sided nanofibers attached and double-stitched with thread according to an embodiment of the present invention as viewed from the side.

In yet an alternative embodiment, the nanofibers 231, 241 may be attached to the panels 310, 320 in both single-sided 412, 422 and double-sided 411, 421 nanofiber areas as shown in FIG. 14A. In this embodiment two of the double-sided nanofiber areas 411, 421 are first placed in contact, then folded over to allow the remaining two double-sided nanofiber areas 411, 421 to attach to the single-sided nanofiber areas 412, 422 as shown in FIG. 14B. Threaded stitching 402, 403 may be added for strength and to form a second nanofiber seam 404 as shown in FIG. 14C.

Figure 15A:
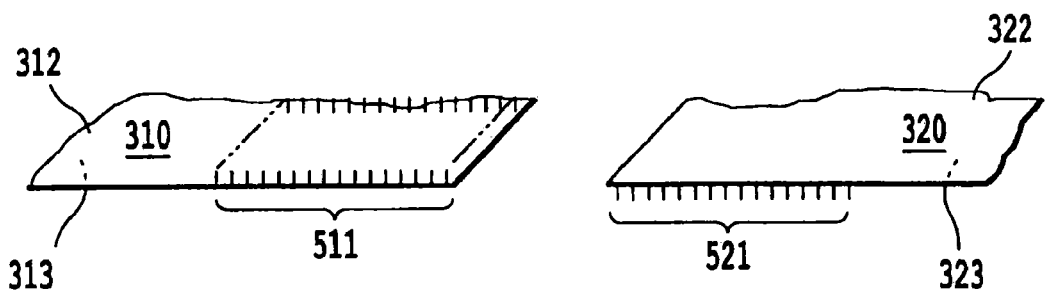
FIG. 15A illustrates a set of two apparel panels having single-sided nanofibers prior to attachment according to an embodiment of the present invention as viewed from the side.
Figure 15B:
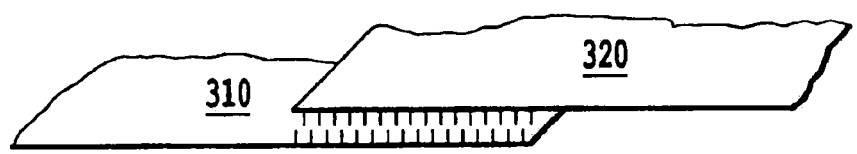
FIG. 15B illustrates the set of two apparel panels having single-sided nanofibers attached according to an embodiment of the present invention as viewed from the side, this FIG. 15B also illustrates the preferred embodiment of the nanofiber zipper.
Figure 15C:
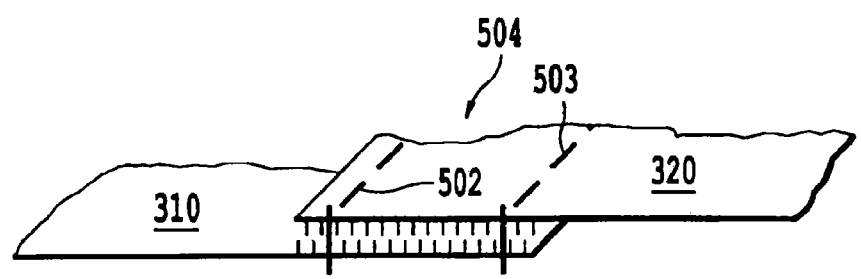
FIG. 15C illustrates the set of two apparel panels having single-sided nanofibers attached and double-stitched with thread according to an embodiment of the present invention as viewed from the side.

In another embodiment, a nanofiber seam 504 may be produced by attaching nanofibers to panels, 310, 320 to form a set of single-sided nanofiber areas 511, 521 as shown in FIG. 15A. The nanofiber panel edges 511,521 are attached together using nanoadhesion by being placed in contact as shown in FIG. 15B. Stitching 502, 503 is applied to add further strength to the nanofibers and thereby produce the nanofiber seam 504 as shown in FIG. 15C.

The nanofiber seams 304, 404, 504, may be used by apparel designers to construct various athletic gear products from one or more woven panels. When the athletic gear is utilized by the final user, the nanofiber seam should keep one or more woven panels reliably together.

In yet another embodiment, the seam arrangement represented by the nanofiber panel edges 511, 521 may be used to reconfigure a pocket on clothing so that the location and the shape of the space that can be accommodated within the pocket may be changed by adjusting the contact area between the panel edges 511 and 521 at a perimeter of the pocket and clothing that the pocket is mounted upon.

In a further embodiment, the seam arrangement represented by the nanofiber panel edges 511, 521 may be used to connect a jacket to pants, e.g., sporting apparel such as running jackets and pants, warm-up jackets and pants, and/or ski jackets and pants. This may improve warmth by keeping the wind out of the area between the jacket and the pants. The panel edge 511 may be on the bottom of the jacket edge and the panel edge 521 may be on the top of the pants as shown in the FIG. 15A. When the pants are attached to the jacket at the panel edges 511, 521, then the panels may create the nanoadhesion attachment as shown in FIG. 15B.

In yet a further embodiment, the seam arrangement represented by the nanofiber panel edges 511, 521 may be used to connect cuff-tabs on shirt sleeves to eliminate the need for buttons.

In another embodiment, the seam arrangement represented by the nanofiber panel edges 511, 521 may be used to adjust the size of air vents in clothing so that the user may decide to enlarge vents during strenuous activity and then reduce the size of the vents after the activity has finished.

In a further embodiment, the seam arrangement represented by the nanofiber panel edges 511, 521 may be used to attach and detach removable clothing elements, such as hoods and sleeves.

In yet another embodiment, the seam arrangement represented by the nanofiber panel edges 511, 521 may be used to attach and detach packaging components so the packaging closure may be curved instead of straight.

Fourth Embodiment—Nanofiber Zipper

Yet another embodiment that may utilize the nanofibers 20 in sporting gear is a nanofiber zipper 600, as shown in the athletic shirt 300 shown earlier in FIG. 12. The zipper may also be adapted for use in athletic gear such as apparel, gym bags, footwear, and the like.

Figure 16A:
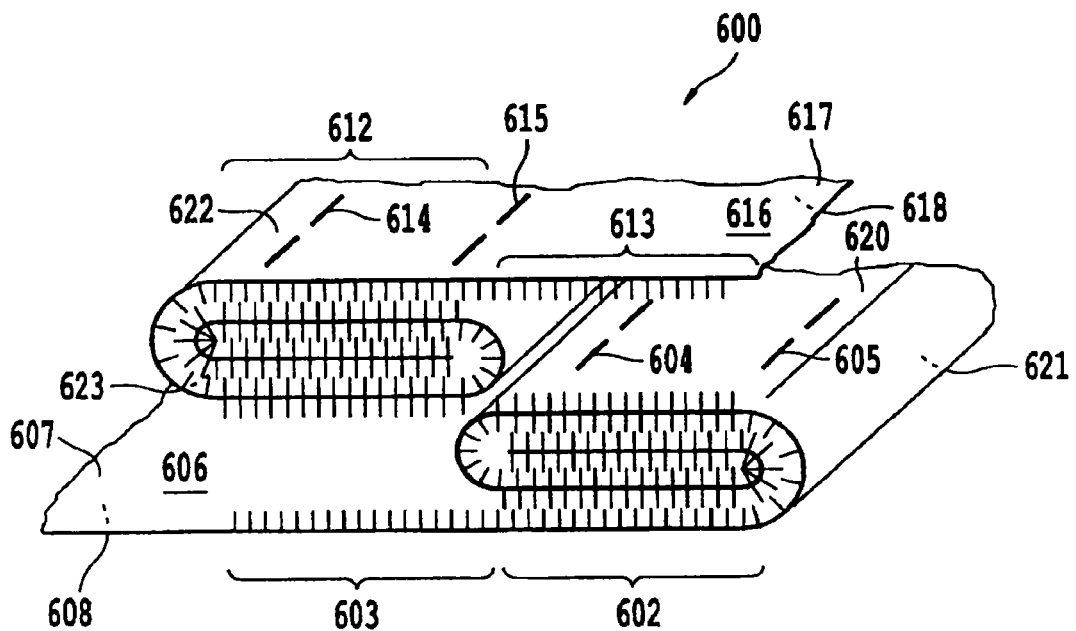
FIG. 16A illustrates first and second nanofiber folds as part of a nanofiber zipper detached in an open state as viewed from the top.
Figure 16B:
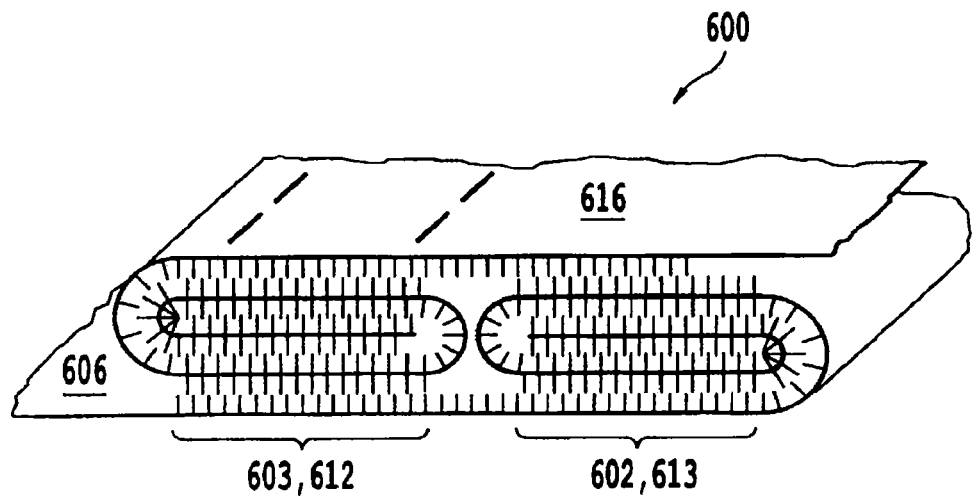
FIG. 16B illustrates first and second nanofiber folds as part of the nanofiber zipper attached in a closed state as viewed from the top.

The nanofiber zipper 600 may be illustrated in FIGS. 12, 16A, 16B and 18C where the nanofiber zipper may be configured to detach a first panel edge 606 from a second panel edge 616 (FIG. 16A) and then later reattach the panels 606, 616 (FIG. 16B). The first panel 606 includes both a top side 607 and a bottom side 608. The second panel 616 includes both a top side 617 and a bottom side 618. The nanofiber zipper 600 may include a zipper slider 630 configured to open and close the zipper, a first nanofiber fold 602 as part of first panel edge 606, a first set of nanofibers 603 attached as part of first panel edge 606, a second nanofiber fold 612 as part of second panel edge 616, and a second set of nanofibers 613 attached as part of second panel edge 616. The nanofiber zipper 600 may include a first set of thread stitches 604, 605 to add strength to the first nanofiber fold 602 and a second set of thread stitches 614, 615 to add strength to the second nanofiber fold 612. The first nanofiber fold 602 may include a top fold side 620 and a bottom fold side 621. The second nanofiber 612 fold may include a top side 622 and a bottom side 623.

The first and second nanofiber folds 602, 612 as well as the first and second nanofibers 603, 613 may be created and attached using the same concepts already discussed as part of the processes used to make the nanofiber seams 304, 404, 504.

Figure 17A:
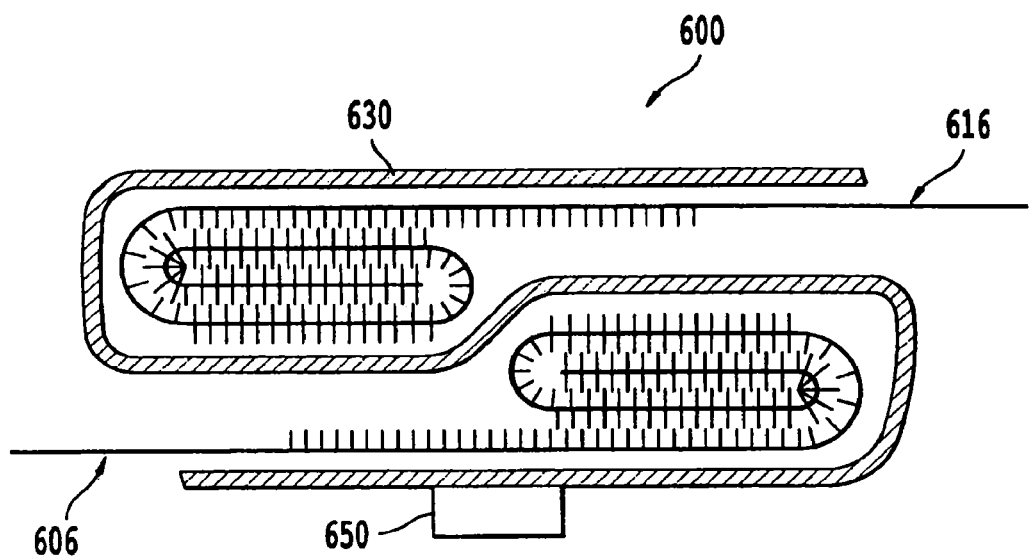
FIG. 17A illustrates a cross section of an upper section of a nanozipper slider showing first and second nanofiber folds as viewed from the top.
Figure 17B:
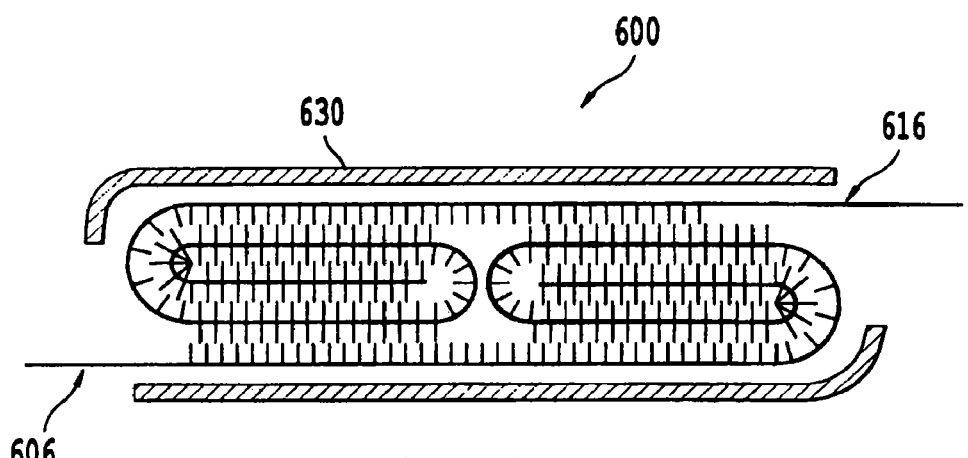
FIG. 17B illustrates a cross section of a lower section of the nanozipper slider showing first and second nanofiber folds as viewed from the top.

FIGS. 16B and 17B show the nanofiber zipper 600 in the closed state where the nanofibers on the first nanofiber fold 602 have attached to the second set of nanofibers 613 using nanoadhesion. Also, the nanofibers on the second nanofiber fold 612 have attached to the first set of nanofibers 603 using nanoadhesion.

Figure 18C:
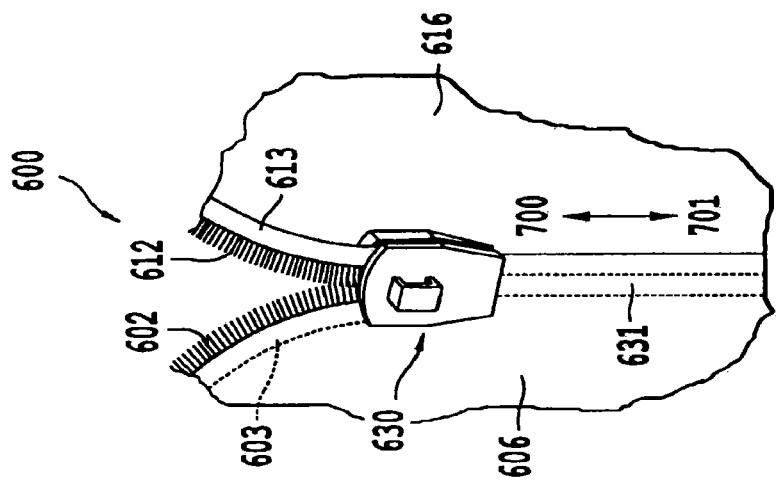
FIG. 18C illustrates the nanofiber zipper slider as part of the full nanofiber zipper.
Figure 18B:
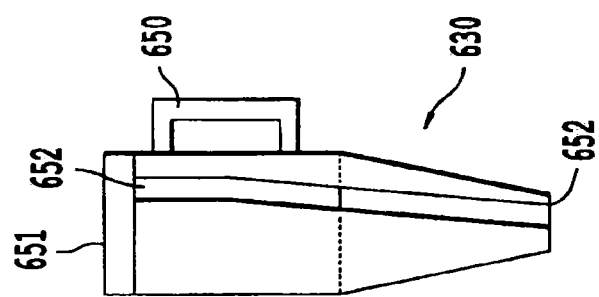
FIG. 18B illustrates the nanofiber zipper slider from the left.

The zipper slider 630 opens and closes the zipper 600 and includes a control handle (not shown) for the user to control the zipper 600. The control handle may be attached at an attachment point 650 as shown in FIGS. 18A, 18B, and 18C.

Figure 18A:
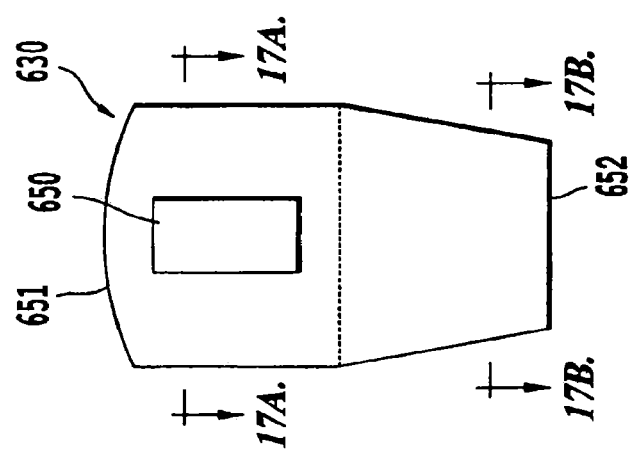
FIG. 18A illustrates the nanofiber zipper slider from the front.

FIGS. 17A and 18A show a cross section at the top 651 of the zipper slider 630 where the panel edges 606, 616 are unattached to each other. The first and second nanofiber folds 602, 612 are used to guide the panel edges 606, 616 through the zipper slider 630. FIG. 17B shows a cross section at the bottom 652 of the zipper slider 630 where the panel edges 606, 616 are attached via nanoadhesion.

A close-up of the zipper slider 630 is shown at FIG. 18A. The slider top 651 is wider than the slider bottom 652. FIG. 18B shows the left side of the zipper slider 630 with an open groove 652 for the first panel edge 606 to travel.

The nanofiber zipper 600 may be supplemented by other fasteners such as traditional hooks or buttons.

The nanofiber zipper 600 is operated by the user by grabbing a control handle (not shown) attached to the 650 attachment at the zipper slider 630. The user moves the zipper slider 630 up 700 along the length of the panel edges 606, 616 to close the zipper 600. The user may open the zipper 600 by moving the zipper slider 630 down 701 along the length of the panel edge 606, 616 and the nanofibers on the panel edges 606, 616 may be pulled apart by the zipper slider. The process is reversible and the zipper 600 may be opened and closed many times.

Although various zipper embodiments are possible with nanoadhesion, the preferred embodiment is shown in FIGS. 15A-15B. The preferred zipper includes panels 310, 320 with nanofibers attached at nanofiber panel edges 511, 512. The nanofiber panel edges 511,521 are attached together using nanoadhesion by being placed in contact as shown in FIG. 15B. The nanofibers panel edges 511, 512 may be later detached by pulling them apart.

Fifth Embodiment—Device Attachment

Yet another embodiment that may utilize the nanofibers 20 in sporting gear is a nanofiber attachment, as demonstrated by a wristwatch 800 in FIG. 19A. The nanofiber attachment may be adapted for other devices other than wristwatches, for example, global positioning system devices, music players or video entertainment devices, communication devices, heart rate monitors, biometric sensors, and the like.

The nanofiber watch 800 may include a strap 801 while worn on the wrist 126 or may be attached to the wrist 126 directly using nanofibers 20 as shown in FIGS. 19B-19D. The watch 800 includes nanofibers 20 that may be attached using one or more of the flocking processes 1, 12 discussed earlier. The watch 800 may be attached directly to the wrist 126 by placing the nanofibers 20 in contact with the 126 or arm 127 to form a nanoadhesion attachment. The wearer engages in whatever activities desired and the nanoadhesion attachment keeps the watch 800 attached to the wrist 126. When the watch 800 is to be removed from the wrist 126, then the wearer may pull the watch 800 away from the wrist 126 to separate the nanofibers 20 from the wrist 126.

Figure 20A:
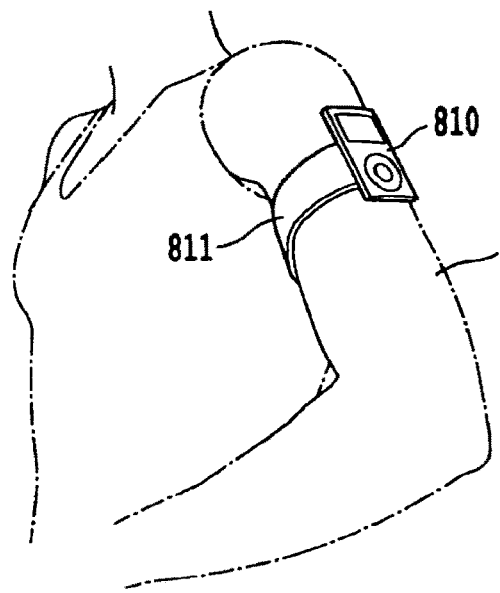
FIG. 20A illustrates a second device attached to an arm using a strap as viewed from the front.
Figure 20B:
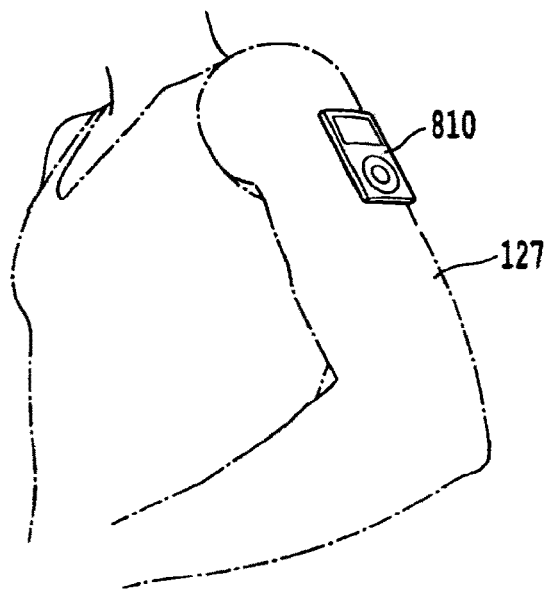
FIG. 20B illustrates the second device watch attached to the arm without the strap as viewed from the front.
Figure 20C:
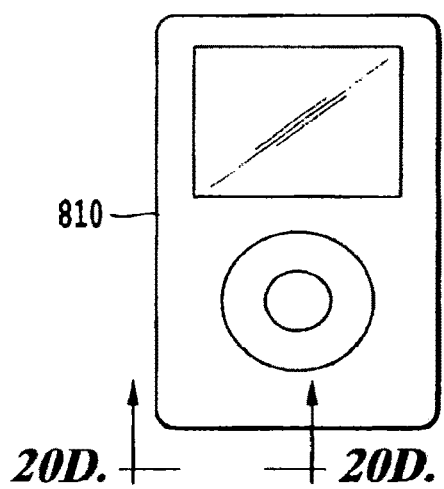
FIG. 20C illustrates the second device as viewed from the front.
Figure 20D:
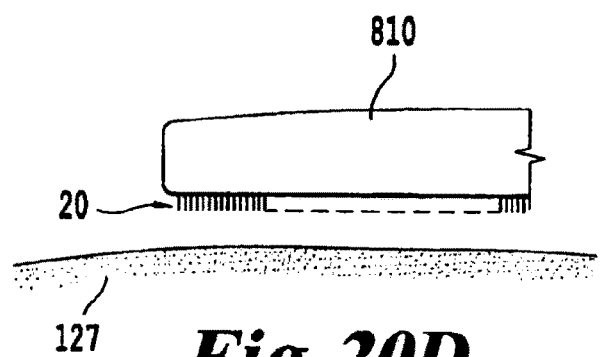
FIG. 20D illustrates the second device with nanofibers attached and the arm as viewed from the side.

A second aspect to the device attachment is to attach a second device 810 to the arm 127 as shown in FIG. 20A-20D. The second device may be a time measuring device, heart monitor, location device, music or video entertainment device, medical sensor, athletic performance measuring sensor, communication device, or the like. The second device 810 may include a strap 811 while worn on the arm 127 or may be attached to the arm 127 directly while solely using nanofibers 20. The second device includes nanofibers 20 that may be attached using one or more of the flocking processes 1, 12 discussed earlier. The second device 810 may be attached directly to the arm 127 by placing the nanofibers 20 in contact with the arm 127 to form a nanoadhesion attachment. The wearer engages in whatever activities desired and the nanoadhesion attachment keeps the second device 810 attached to the arm 127. When the second device 810 is to be removed from the arm 127, then the wearer may pull the second device 810 away from the arm 127 to separate the nanofibers 20 from the arm 127 as shown in FIG. 20D.

Figure 21A:
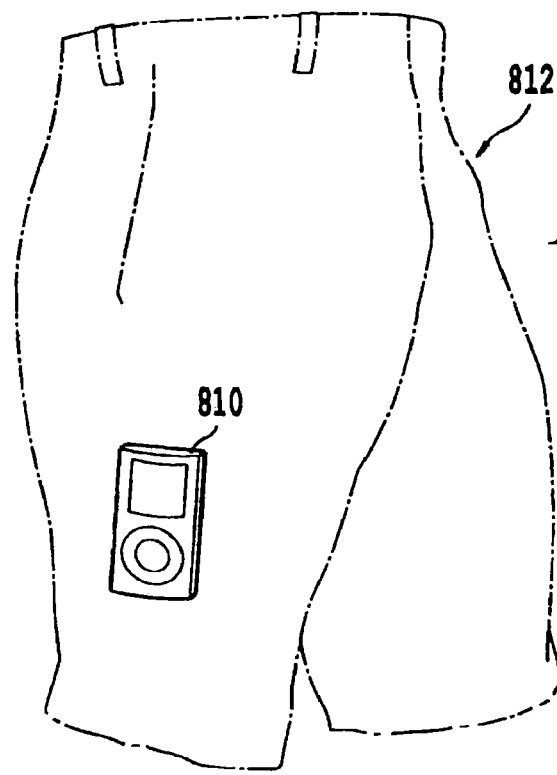
FIG. 21A illustrates the second device attached directly to a piece of clothing using nanofibers as viewed from the front.
Figure 21C:
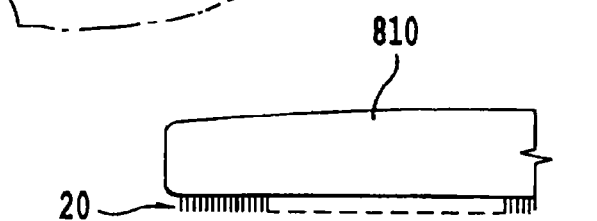
FIG. 21C illustrates the second device with nanofibers attached and the piece of clothing as viewed from the side.
Figure 21B:
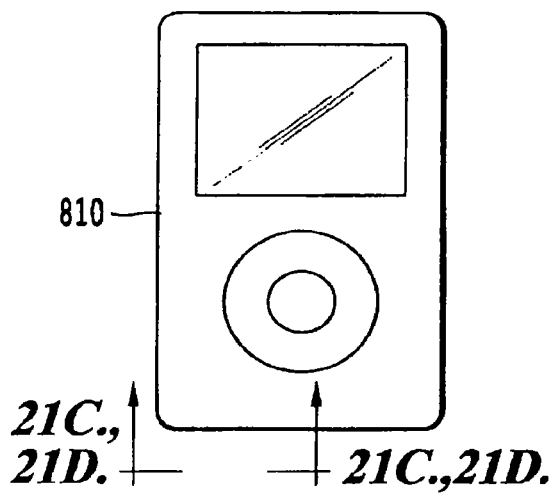
FIG. 21B illustrates the second device as viewed from the front.

In a third aspect to the device attachment embodiment, a second device 810 is attached to a piece of clothing 812 as shown in FIGS. 21A-21C. The second device 810 may be attached directly to the clothing 812. The user merely attaches the second device 810 to the clothing 812 so that the nanofibers 20 on the device 810 come in contact with the clothing 812 to form a nanoadhesion attachment. When the second device 810 is to be removed from the clothing 812, then the wearer may pull the second device 810 away from the clothing 812 to separate the nanofibers 20 from the clothing 812 as shown in FIG. 21C. The piece of clothing 812 may be shirts, pants, socks, shoes, jackets, or the like.

In yet a fourth aspect to the device attachment embodiment, the second device 810 is attached to a piece of clothing 812 having nanofibers 815 attached to the clothing 812. In this aspect a nanoadhesion attachment is formed between the nanofibers 20 attached to the second device 810 and the nanofibers 815 attached to the clothing 812 using the one or more of the flocking processes described earlier. The user merely attaches the second device 810 to the clothing 812 so that the nanofibers 20 on the device 810 and the nanofibers 815 on the clothing 812 come in contact with each other to form a nanoadhesion attachment. The user engages in whatever activity is desired and the nanoadhesion attachment keeps the device 810 attached to the clothing 812. When the second device 810 is to be removed from the clothing 812, then the wearer may pull the second device 810 away from the clothing 812 to separate the nanofibers 20, 815 as shown in FIG. 21D.

Figure 21D:
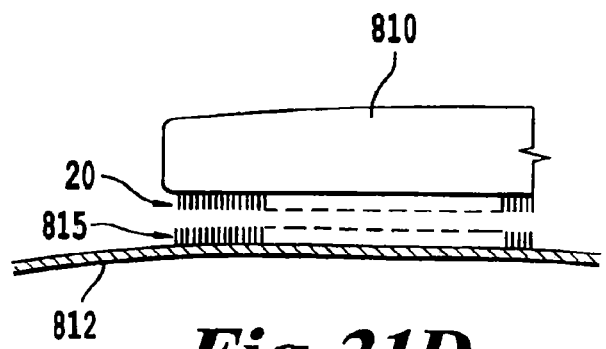
FIG. 21D illustrates the second device with nanofibers attached and the piece of clothing with nanofibers attached as viewed from the side.

In yet a fifth aspect to the device attachment embodiment, the second device 810 illustrated in either FIG. 21C or 21D could be a component designed to cushion the impact of certain body parts during sporting activities. The component could be functionally equivalent to shin pads used by soccer players, modular protection zones used by football players on football pants and other protective gear, or localized padding used in biking shorts used by cyclists to lessen the shock and bumps from a bicycle seat to contact points on the human body. The component may have nanofibers 20 attached to the component and may have nanofibers 815 attached to the contact area on the clothing.

In yet a sixth aspect to the device attachment embodiment, the second device 810 may be a backpack and a set of associated straps that may be attached to a wearer's clothing using nanofibers 20 attached to the associated straps. The nanofibers 20 may be attached to nanofibers 815 on the wearer's clothing to form a nanoadhesion attachment. An advantage of using nanofibers 20, 815 to attach the straps to the clothing may be to reduce chafing during activity. Other embodiments may have a backpack without straps and the backpack attached directly to the clothing with a nanoadhesion attachment.

In a seventh embodiment, a bottle closure (broadly represented as element 810 in FIG. 21C) may have nanofibers 20 to form a nanoadhesion attachment with a bottle (broadly represented as element 812 in FIG. 21C) to replace threaded closures used on bottles, such as soda cans, water bottles, and the like.

In an eighth embodiment, a roof rack may to interface with an automobile (the roof rack broadly represented as element 810 in FIG. 21C) may have nanofibers 20 to form a nanoadhesion attachment with an exterior surface of an automobile (broadly represented as element 812 in FIG. 21C). The roof rack may be used to transport bicycles, boats, sporting equipment, packages in transit, or the like.

In a ninth embodiment, a clothing hanger (the hanger is broadly represented as element 810 in FIG. 21C) may have nanofibers 20 to form a nanoadhesion attachment with clothing that is desired to be hung from the hanger (the clothing broadly represented as element 812 in FIG. 21C). The clothing may or may not have nanofibers to attach with those nanofibers 20 on the hanger.

In a tenth embodiment, a clothing price tag or information tag (the tag is broadly represented as element 810 in FIG. 21C) may have nanofibers 20 to form a nanoadhesion attachment with clothing that the tag is associated with (the clothing broadly represented as element 812 in FIG. 21C).

In an eleventh embodiment, a portion of a surface of a glove (the portion of the glove surface is broadly represented as element 810 in FIG. 21C) may have nanofibers 20 to form a nanoadhesion attachment with an item that the glove is gripping while the glove is in the user's hand (the item is broadly represented as element 812 in FIG. 21C). The item may be a basketball, water polo ball, a hockey stick, a tennis racquet, or other item similarly to be gripped by a glove.

In a twelfth embodiment, a gripping surface (the gripping surface broadly represented as element 810 in FIG. 21C) may have nanofibers 20 to form a nanoadhesion attachment with a surface of a hand or glove (the surface of the hand or glove broadly represented as element 812 in FIG. 21C). The gripping surface may be a hockey stick gripping area, a tennis racquet grip, or other surface similarly gripped by a glove or hand. The glove may also have nanofibers 20 attached to interface with the nanofibers on the gripping surface.

Further, it should be appreciated that the exemplary embodiments of the invention are not limited to the exemplary embodiments shown and described above. While this invention has been described in conjunction with exemplary embodiments outlined above, various alternatives, modifications, variations and/or improvements, whether known or that are, or may be, presently unforeseen, may become apparent. Accordingly, the exemplary embodiments of the invention, as set forth above are intended to be illustrative, not limiting. The various changes may be made without departing from the spirit and scope of the invention. Therefore, the systems and methods according to exemplary embodiments of this invention are intended to embrace all now known or later-developed alternatives, modifications, variations and/or improvements.

Obviously, numerous modifications and variations of the present invention are possible in light of the above teachings. It is therefore to be understood that within the scope of the appended claims, the invention may be practiced otherwise than as specifically described herein.

What is claimed is:

1. An article of apparel comprising:
    a first fabric panel comprising:
        an edge,
        a top surface having a first portion disposed proximate to the edge and a second portion disposed on a side of the first portion opposite of the edge,
        a bottom surface,
        a first set of nanofibers disposed on the first portion of the top surface of the first fabric panel, and
        a first fold of the first fabric panel disposed between the first portion of the first fabric panel and the second portion of the first fabric panel such that the first portion of the first fabric panel is folded over onto the second portion of the top surface of the first fabric panel; and
    a second fabric panel removably coupled to the first fabric panel, the second fabric panel comprising:
        an edge,
        a top surface,
        a bottom surface having a third portion disposed proximate to the edge and a fourth portion disposed on a side of the first portion opposite of the edge,
        a second set of nanofibers disposed on the third portion of the bottom surface of the second fabric panel, and
        a second fold of the second fabric panel disposed between the third portion of the second fabric panel and the fourth portion of the second fabric panel such that the third portion of the second fabric panel is folded over onto the fourth portion of the bottom surface of the second fabric panel, wherein the third portion of the second fabric panel abuts the first portion of the first fabric panel so that the first set of nanofibers couples to the second set of nanofibers via nanoadhesion, the first portion of the first fabric panel being disposed between the third portion of the second fabric panel and the fourth portion of the second fabric panel, and the third portion of the second fabric panel being disposed between the first portion of the first fabric panel and the second portion of the first fabric panel.

2. The article of apparel of claim 1, wherein each nanofiber in the first set of nanofibers is generally perpendicular to the top surface of the first fabric panel and each nanofiber in the second set of nanofibers is generally perpendicular to the bottom surface of the second fabric panel.

3. The article of apparel of claim 1, further comprising:
at least one set of stitching disposed along an abutment of the first portion to the third portion.

4. The article of apparel of claim 1, wherein the first fabric panel further comprises:
a third set of nanofibers disposed on a fifth portion of the bottom surface of the first fabric panel, the fifth portion being disposed proximate to the edge of the first fabric panel, and the fifth portion and the third set of nanofibers being disposed opposite the first portion and the first set of nanofibers; and
a fourth set of nanofibers disposed on the second portion of the top surface of the first fabric panel.

5. The article of apparel of claim 4, wherein the second fabric panel further comprises:
a fifth set of nanofibers disposed on a sixth portion of the top surface of the second fabric panel, the sixth portion being disposed proximate to the edge of the second fabric panel, and the sixth portion and the fifth set of nanofibers being disposed opposite the third portion and the second set of nanofibers; and
a sixth set of nanofibers disposed on the fourth portion of the bottom surface of the second fabric panel.

6. The article of apparel of claim 5, wherein when the second fabric panel is removably coupled to the first fabric panel, the third set of nanofibers couples to the sixth set of nanofibers via nanoadhesion, and the fourth set of nanofibers couples to the fifth set of nanofibers via nanoadhesion.

7. The article of apparel of claim 1, wherein the first fabric panel is a first fabric panel of a shirt and the second fabric panel is a second fabric panel of the shirt.

8. The article of apparel of claim 1, wherein the edge of the first fabric panel is a bottom edge of a shirt, and the edge of the second fabric panel is a top edge of a pair of pants.

9. The article of apparel of claim 1, wherein the edge of the first fabric panel is a first edge of a cuff on a shirt sleeve, and the edge of the second fabric panel is a second edge of the cuff of the shirt sleeve.

10. The article of apparel of claim 1, wherein the second fabric panel is a pocket.

11. The article of apparel of claim 1, wherein the first fabric panel is a fabric panel of a shirt and the second fabric panel is a hood.

12. The article of apparel of claim 1, wherein the first fabric panel is a fabric panel of a body of a shirt and the second fabric panel is a sleeve.

13. The article of apparel of claim 1, wherein the first fabric panel is a fabric panel of a shirt that includes at least one opening and the second fabric panel is a reconfigurable vent disposed proximate to the at least one opening to alter a size of at least one openings of the shirt.

14. An article of apparel comprising:
a first fabric panel comprising:
a top surface,
a bottom surface,
a first set of fabric folds forming a first edge, the first set of fabric folds forming a plurality of folds of the first fabric panel,
a first set of nanofibers disposed on the top surface of the first fabric panel and the bottom surface of the first fabric panel within the first set of fabric folds, and
a second set of nanofibers disposed on the top surface proximate to the first set of fabric folds; and
a second fabric panel removably coupled to the first fabric panel, the second fabric panel comprising:
a top surface,
a bottom surface,
a second set of fabric folds forming a second edge, the second set of fabric folds forming a plurality of folds of the second fabric panel,
a third set of nanofibers disposed on the top surface of the second fabric panel and the bottom surface of the second fabric panel within the second set of fabric folds, and
a fourth set of nanofibers disposed on the bottom surface proximate to the second set of fabric folds,
wherein, when the second fabric panel is removably coupled to the first fabric panel, a portion of the first set of nanofibers couples to the fourth set of nanofibers via nanoadhesion and a portion of the third set of nanofibers couples to the second set of nanofibers via nanoadhesion, the first set of fabric folds being disposed between the top surface of the first fabric panel and the bottom surface of the second fabric panel, the second set of fabric folds being disposed between the bottom surface of the second fabric panel and the top surface of the first fabric panel, and a first fold of the first set of fabric folds is in abutment with a second fold of the second set of fabric folds.

* * * * *